(12) United States Patent
Beaulieu et al.

(10) Patent No.: US 7,189,716 B2
(45) Date of Patent: Mar. 13, 2007

(54) TYROSINE KINASE INHIBITORS

(75) Inventors: Francis Beaulieu, LaPrairie (CA); Carl Ouellet, Boucherville (CA); Kurt Zimmermann, Durham, CT (US); Upender Velaparthi, North Haven, CT (US); Mark D. Wittman, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 397 days.

(21) Appl. No.: 10/751,798

(22) Filed: Jan. 5, 2004

(65) Prior Publication Data

US 2004/0180897 A1 Sep. 16, 2004

Related U.S. Application Data

(60) Provisional application No. 60/437,926, filed on Jan. 3, 2003.

(51) Int. Cl.
*A61K 31/5377* (2006.01)
*C07D 413/14* (2006.01)

(52) U.S. Cl. .................... 514/234.2; 544/127
(58) Field of Classification Search ............... 544/127; 514/234.2

See application file for complete search history.

(56) References Cited

U.S. PATENT DOCUMENTS 6,465,484 B1 10/2002 Bilodeau et al.

2002/0103230 A1 8/2002 Renhowe et al.

FOREIGN PATENT DOCUMENTS

| DE | 3722992 A1 * | 1/1989 |
| JP | 63-230687 | 9/1988 |
| WO | WO 02/079192 A1 | 10/2002 |

OTHER PUBLICATIONS

U.S. Appl. No. 10/263,448, filed Oct. 2, 2002, Wittman et al.
U.S. Appl. No. 10/674,098, filed Sep. 29, 2003, Velaparthi et al.

* cited by examiner

*Primary Examiner*—Rebecca Anderson
(74) *Attorney, Agent, or Firm*—Elliot Korsen; Maureen S. Gibbons

(57) ABSTRACT

The present invention provides compounds of formula I

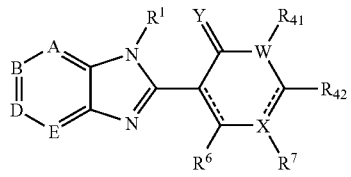

and pharmaceutically acceptable salts thereof. The formula I compounds inhibit tyrosine kinase enzymes thereby making them useful as anti-cancer agents.

11 Claims, No Drawings

TYROSINE KINASE INHIBITORS

RELATED APPLICATIONS

This application claims priority benefit under Title 35 § 119(e) of U.S. provisional Application No. 60/437,926, filed Jan. 3, 2003, the contents of which are incorporated by reference.

FIELD OF INVENTION

The present invention relates generally to the field of tyrosine kinase enzyme inhibition using novel small molecules.

BACKGROUND OF THE INVENTION

Tyrosine Kinases are a class of enzymes, which catalyze the transfer of the terminal phosphate of adenosine triphosphate to the phenolic hydroxyl group of a tyrosine residue present in the target protein. Tyrosine kinases play a critical role in signal transduction for several cellular functions including cell proliferation, carcinogenesis, apoptosis, and cell differentiation (Plowman, G. D.; Ullrich, A.; Shawver, L. K.: Receptor Tyrosine Kinases As Targets For Drug Intervention. *DN&P* (1994) 7: 334–339). Therefore inhibitors of these enzymes would be useful for the treatment or prevention of proliferative diseases which are dependent on these enzymes. Strong epidemiologic evidence suggests that the overexpression or activation of receptor protein tyrosine kinases leading to constitutive mitogenic signaling is an important factor in a growing number of human malignancies. Tyrosine kinases that have been implicated in these processes include Abl, CDK's, EGF, EMT, FGF, FAK, Flk-1/KDR, HER-2, IGF-1R, IR, LCK, MEK, MET, PDGF, Src, and VEGF (Traxler, P. M. Protein Tyrosine Kinase Inhibitors in Cancer Treatment. *Exp. Opin. Ther. Patents* (1997) 7: 571–588; incorporated herein by reference). Hence, there is an ongoing need to investigate novel compounds that can be used to regulate or inhibit tyrosine kinase enzymes.

SUMMARY OF THE INVENTION

The present invention relates to compounds which inhibit tyrosine kinase enzymes, compositions which contain tyrosine kinase inhibiting compounds and methods of using inhibitors of tyrosine kinase enzymes to treat diseases which are characterized by an overexpression or upregulation of tyrosine kinase activity such as cancer, diabetes, restenosis, arteriosclerosis, psoriasis, angiogenic diseases and immunologic disorders (Powis, G.; Workman, P. Signaling targets For The Development of Cancer Drugs. *Anti-Cancer Drug Design* (1994), 9: 263–277; Merenmies, J.; Parada, L. F.; Henkemeyer, M. Receptor Tyrosine Kinase Signaling in Vascular Development. *Cell Growth Differ* (1997) 8: 3–10; Shawver, L. K.; Lipsosn, K. E.; Fong, T. A. T.; McMahon, G.; Plowman, G. D.; Strawn, L. M. Receptor Tyrosine Kinases As Targets For Inhibition of Angiogenesis. *Drug Discovery Today* (1997) 2: 50–63; all herein incorporated by reference).

In addition to being used as single agents, it is contemplated that tyrosine kinase inhibitors can enhance the activity of cytotoxic or cytostatic treatments when used in combination with standard therapies known in the art.

The present invention is directed to compounds having Formula I

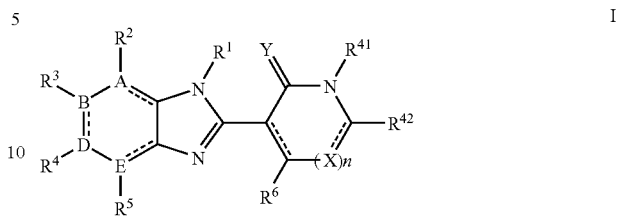

its enantiomers, diastereomers, pharmaceutically acceptable salts, hydrates, prodrugs and solvates thereof;

wherein

A, B, D, and E are each, independently, C or N provided that if A, B, D, and E are each C, then one of $R^2$ and $R^3$, $R^3$ and $R^4$, or $R^4$ and $R^5$ is taken together to form a heterocyclic ring having at least one nitrogen atom;

X is selected from the group consisting of N or C wherein each of said N or C may be optionally substituted, independently, with $R^7$ and n is 0, 1, 2, or 3;

Y is selected from the group consisting of O and S;

W is selected from the group consisting of N, C, O, and S, provided that when W is O or S, $R^{41}$ is absent;

$R^1$, $R^2$, $R^3$, $R^4$, $R^5$, $R^6$, $R^7$, $R^{41}$, and $R^{42}$ are each independently selected from the group consisting of H, $C_{1-6}$ alkyl, alkenyl, alkynyl, cycloalkyl, heterocycloalkyl, halo, amino, aminoalkyl, alkoxy, thioalkoxy, nitro, aryl, heteroaryl, alkoxyalkyl, thioalkoxyalkyl, aminoalkyl, aralkyl, heteroarylalkyl, heterocycloalkylalkyl, —CN, —$CO_2R^8$, —$CONR^9R^{10}$, —$CO_2NR^{11}R^{12}$, —$NR^{13}CONR^{14}R^{15}$, —$NR^{16}SO_2R^{17}$, —$SO_2NR^{18}R^{19}$, —$C(NR^{20})NR^{21}R^{22}$, —NH-Z, —NH-Z-aryl, and NH-Z-heteroaryl, or any two of $R^2$ and $R^3$, $R^3$ and $R^4$, or $R^4$ and $R^5$ can be taken together to form a heterocyclic ring having at least one nitrogen atom;

Z is selected from the group consisting of $C_1$–$C_6$ alkyl, cycloalkyl, alkenyl, cycloalkenyl, and alkynyl; Z optionally having one or more hydroxy, thiol, alkoxy, thioalkoxy, amino, halo, $NR^{23}SO_2R^{24}$ groups; Z optionally incorporating one or more groups selected from the group consisting of —CO, —CNOH, —$CNOR^{26}$, —$CNNR^{27}$, —$CNNCOR^{28}$ and —$CNNSO_2R^{29}$;

$R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, and $R^{26}$ are independently selected from the group consisting of H, alkyl, alkenyl, alkynyl, cycloalkyl, cycloalkylalkyl, hydroxy, alkoxy, aryl, heteroaryl, heterocyclyl, heteroarylalkyl, and alkyl-$R^{25}$ wherein $R^{25}$ is alkenyl, hydroxy, thiol, alkoxy, thioalkoxy, amino, alkylamino, dialkylamino, aryl, heteroaryl, cyano, halo, heteroaryl, heterocyloalkyl, sulfoxy, sulfonyl, —$NR^{27}COOR^{28}$, —$NR^{29}C(O)R^{30}$, —$NR^{31}SO_2R^{32}$, $SO_2NR^{31}R^{32}$, —$C(O)NR^{33}R^{34}$, and;

$R^{27}$, $R^{28}$, $R^{29}$, $R^{30}$, $R^{31}$, $R^{32}$, $R^{33}$ and $R^{34}$ are, independently, hydrogen, alkyl, or cycloalkyl.

The invention also provides a pharmaceutical composition comprising a compound of formula I, as defined above, and a pharmaceutically acceptable carrier.

The invention further provides a pharmaceutical composition comprising a compound of formula I, as defined above, in combination with pharmaceutically acceptable carrier and at least one other anti-cancer agent optionally formulated as a fixed dose.

Additionally provided is a method of treating a condition associated with at least one tyrosine kinase enzyme comprising administering to a mammalian species in need of such treatment an effective amount of a compound of formula I, as defined above. Furthermore, the invention provides a method of treating a condition associated with at least one tyrosine kinase enzyme comprising administering to a mammalian species at least one other anti-cancer agent in combination with a compound of formula I, as defined above.

The invention also provides for methods for treating proliferative diseases, such as cancer, comprising administering to a mammal in need of such treatment a therapeutically effective amount of a compound having Formula I.

DESCRIPTION

The present invention provides for compounds of formula I, as defined above, pharmaceutical compositions employing such compounds and methods of using such compounds.

Listed below are definitions of various terms used to describe the compounds of the instant invention. These definitions apply to the terms as they are used throughout the specification (unless they are otherwise limited in specific instances) either individually or as part of a larger group.

The term "alkyl" herein alone or as part of another group refers to a monovalent alkane (hydrocarbon) derived radical containing from 1 to 12 carbon atoms unless otherwise defined. An alkyl group is an optionally substituted straight, branched or cyclic saturated hydrocarbon group. A straight chain alkyl group preferably contains from 1 to 6 carbon atoms. When substituted, alkyl groups may be substituted with up to four substituent groups, at any available point of attachment. When the alkyl group is said to be substituted with an alkyl group, this is used interchangeably with "branched alkyl group". Exemplary alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents may include but are not limited to one or more of the following groups: hydroxy, halo (such as F, Cl, Br, I), haloalkyl (such as $CCl_3$ or $CF_3$), alkoxy, alkylthio, cyano, carboxy (—COOH), alkylcarbonyl (—C(O)R), alkoxycarbonyl (—OCOR), amino, carbamoyl (—NHCOOR or —OCONHR), urea (—NHCONHR), thiol, (—SH), sulfoxy, sulfonyl, aryl, heteroaryl, and heterocycloalkyl. Alkyl groups as defined may also comprise one or more carbon to carbon double bonds or one or more carbon to carbon triple bonds. Alkyl groups may also be represented by the formula alkyl-$R^{25}$. In preferred embodiments, the alkyl group is a methyl, ethyl, propyl or butyl group and includes substituted methyl, ethyl, propyl or butyl groups.

The term "alkenyl" herein alone or as part of another group refers to a hydrocarbon radical straight, branched or cyclic containing from 2 to 12 carbon atoms and at least one carbon to carbon double bond. An alkenyl group may be optionally substituted in the same manner as described for an alkyl group.

The term "alkynyl" herein alone or as part of another group refers to a hydrocarbon radical straight, branched or cyclic containing from 2 to 12 carbon atoms and at least one carbon to carbon triple bond. An alkynyl group may be optionally substituted in the same manner as described for an alkyl group.

The term "alkoxy" as used alone or in combination herein refers to a straight or branched chain alkyl group covalently bonded to the parent molecule through an oxygen atom linkage containing from one to ten carbon atoms and the terms "$C_{1-6}$ alkoxy" and "lower alkoxy" refer to such groups containing from one to six carbon atoms. Examples include, but are not limited to, methoxy, ethoxy, propoxy, isopropoxy, butoxy, t-butoxy and the like. The term "optionally substituted" when used in connection with an alkoxy substituent refers to the replacement of up to two hydrogens, preferably on different carbon atoms with a radical selected from the group of lower alkyl, phenyl, cyano, halo, trifluoromethyl, nitro, hydroxy, alkanoyl, amino, monoalkyl amino and dialkylamino. Alkoxy groups may be substituted in the same manner that alkyl groups can be substituted as described above.

The term "sulfoxy" herein alone or as part of a group refers to —SO and may be substituted with, for example, alkyl, aryl or heteroaryl groups.

The term "sulfonyl" herein alone or as part of a group refers to —$SO_2$ and may be substituted with alkyl, aryl or heteroaryl groups.

The term "amino" herein alone or as part of another group refers to —$NH_2$. An "amino" may optionally be substituted with one or two substituents, which may be the same or different, such as alkyl, aryl, arylalkyl, alkenyl, alkynyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. Preferred substituents include alkylamino and dialkylamino, such as methylamino, ethylamino, dimethylamino, and diethylamino. These substituents may be further substituted with a carboxylic acid or any of the alkyl or aryl substituents set out herein. In addition, the amino substituents may be taken together with the nitrogen atom to which they are attached to form 1-pyrrolidinyl, 1-piperidinyl, 1-azepinyl, 4-morpholinyl, 4-thiamorpholinyl, 4-sulfoxymorpholine, 4-sulfonylmorpholine, 1-piperazinyl, 4-alkyl-1-piperazinyl, 4-arylalkyl-1-piperazinyl, 4-diarylalkyl-1-piperazinyl, 1-homopiperazinyl, 4-alkyl-1-homopiperazinyl, 4-arylalkyl-1-homopiperazinyl, 4-diarylalkyl-1-homopiperazinyl; 1-pyrrolidinyl, 1-piperidinyl, or 1-azepinyl, optionally substituted with alkyl, alkoxy, alkylthio, halo, trifluoromethyl or hydroxy.

The term "aryl" herein alone or as part of another group refers to monocyclic or bicyclic aromatic rings, e.g. phenyl, substituted phenyl and the like, as well as groups which are fused, e.g., napthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Aryl groups may optionally be substituted with one or more groups including, but not limited to halogen, alkyl, alkenyl, alkynyl, alkoxy, hydroxy, carboxy, carbamoyl, alkyloxycarbonyl, alkylaminocarbonyl, nitro, trifluoromethyl, amino, cycloalkyl, cyano, alkyl $S(O)_m$ (m=0, 1, 2), or thiol. Aryl groups may also be substituted with heterocycloalkyl and heterocycloaryl groups to form fused rings, such as dihydrobenzfuranyl, oxindolyl, indolyl, indolinyl, oxindolyl, benzoxazolidinonyl, benzoxazolinyl and benzoxazolidinone.

The term "cycloalkyl" herein alone or as part of another group refers to fully saturated and partially unsaturated hydrocarbon rings of 3 to 9, preferably 3 to 7 carbon atoms. Further, a cycloalkyl may be substituted. A substituted cycloalkyl refers to such rings having one, two, or three substituents, preferably one, selected from the group consisting of halo, alkyl, substituted alkyl, alkenyl, alkynyl, nitro, cyano, oxo (=O), hydroxy, alkoxy, thioalkyl, —CO₂H, —OC(=O)H, CO₂-alkyl, —OC(=O)alkyl, =N—OH, =N—O-alkyl, aryl, heteroaryl, heterocyclo, a five or six membered ketal (i.e. 1,3-dioxolane or 1,3-dioxane), —NR'R", —C(=O)NR'R", —OC(=O)NR'R", —NR'CO₂'R", —NR'C(=O)R", —SO₂NR'R", and —NR'SO₂R", wherein each of R' and R" is independently selected from hydrogen, alkyl, substituted alkyl, and cycloalkyl, or R' and R" together form a heterocyclo or heteroaryl ring. Cycloalkyl groups may also be substituted with hetero atoms such as O, N, and S to form heterocycloalkyl groups. Preferred heterocycloalkyl groups include optionally substituted morpholine, homomorpholine (7 membered ring), thiomorpholine, piperazine, homopiperazine (7 membered ring), and piperidine.

The term "heteroaryl" herein alone or as part of another group refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or nonaromatic. The heteroaryl group may be attached at any available nitrogen or carbon atom of any ring. The heteroaryl ring system may contain zero, one, two or three substituents selected from the group consisting of halo, alkyl, substituted alkyl, alkenyl, alkynyl, nitro, cyano, hydroxy, alkoxy, thioalkyl, —CO₂H, —OC(=O)H, —CO₂-alkyl, —OC(=O) alkyl, phenyl, benzyl, phenylethyl, phenyloxy, phenylthio, cycloalkyl, substituted cycloalkyl, heterocyclo, heteroaryl, —NR'R", —C(=O)NR'R", —OC(=O)NR'R", —NR'CO₂'R", —NR'C(=O)R", —SO₂NR'R", and —NR'SO₂R", wherein each of R' and R" is independently selected from hydrogen, alkyl, substituted alkyl, and cycloalkyl, or R' and R" together form a heterocyclo or heteroaryl ring.

Exemplary monocyclic heteroaryl groups include pyrrolyl, pyrrolidinyl, imidazolinyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl, and the like.

Exemplary bicyclic heteroaryl groups include indolyl, indolinyl, oxindolyl, benzoxazolidinone, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzindolyl, phenanthrollinyl, acridinyl, phenanthridinyl, xanthenyl and the like.

The term "halogen" or "halo" herein alone or as part of another group refers to chlorine, bromine, fluorine or iodine selected on an independent basis.

The term "hydroxy" herein alone or as part of another group refers to —OH.

The term "thioalkoxy" herein alone or as part of another group refers to an alkyl group as defined herein attached to the parent molecular group through a sulfur atom. Examples of thioalkoxy include, but are not limited to, thiomethoxy, thioethoxy, and the like.

Abbreviations: "Ph" represents phenyl; "Me" represents methyl; and "Et" represents ethyl.

An "anti-cancer agent" as used herein includes known anti-cancer treatments such as radiation therapy or with cytostatic or cytotoxic agents, such as for example, but not limited to, DNA interactive agents, such as cisplatin or doxorubicin; topoisomerase II inhibitors, such as etoposide; topoisomerase I inhibitors such as irinotecan or topotecan; tubulin interacting agents, such as paclitaxel, docetaxel or the epothilones; hormonal agents, such as tamoxifen; thymidilate synthase inhibitors, such as 5-fluorouracil; antimetabolites, such as methotrexate; tyrosine kinase inhibitors such as IRESSA(gefitinib) and TARCEVA(erlotinib); angiogenesis inhibitors; EGF inhibitors; VEGF inhibitors; CDK inhibitors; Her1/2 inhibitors and monoclonal antibodies directed against growth factor receptors such as erbitux (EGF), HERCEPTIN(trastuzumab) (Her2), or avastin (VEGF).

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al., *Protective Groups in Organic Synthesis*, Wiley, N.Y. (1991).

When $C_{1-6}$ alkyl, alkenyl, alkynyl, cycloalkyl are substituted, they are preferably substituted with one or more hydroxy, cyano, carbamoyl, hydroxy, alkoxy, thiol, alkenyl, thioalkoxy, amino, alkylamino, amido, sulfonyl, sulfoxy, sulfonamido, halo, heterocycloalkyl, aryl or heteroaryl.

When aryl or heteroaryl are substituted, they are preferably substituted with one or more alkyl, alkenyl, alkynyl, cyano, carbamoyl, hydroxy, alkoxy, thioalkoxy, amino, amido, sulfonamido, halo or with $R^{40}$, R" wherein $R^{40}$, R" form a ring that is fused to the aryl group. When CH₂aryl or heteroaryl are substituted, they are preferably substituted with one or more alkyl, alkenyl, alkynyl, cyano, carbamoyl, hydroxy, alkoxy, thioalkoxy, amino, amido, sulfonamido, or halogen.

When NH-Z-aryl or NH-Z-heteroaryl groups are substituted, they are preferably substituted with one or more alkyl, alkenyl, alkynyl, hydroxy, alkoxy, thioalkoxy, amino, halogen, nitro, nitrile, carboxylate, alkoxycarbonyl, carbamoyl, ester, amide, aryl, or heteroaryl groups.

The numbers in the subscript after the symbol "C" define the number of carbon atoms a particular group can contain. For example "$C_{1-6}$ alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl. Depending on the context, "$C_{1-6}$ alkyl" can also refer to $C_{1-6}$ alkylene which bridges two groups; examples include propane-1,3-diyl, butane-1,4-diyl, 2-methyl-butane-1,4-diyl, etc. "$C_{2-6}$ alkenyl" means a straight or branched carbon chain having at least one carbon-carbon double bond, and having from two to six carbon atoms; examples include ethenyl, propenyl, isopropenyl, butenyl, isobutenyl, pentenyl, and hexenyl. Depending on the context, "$C_{2-6}$ alkenyl" can also refer to $C_{2-6}$ alkenediyl which bridges two groups; examples include ethylene-1,2-diyl (vinylene), 2-methyl-2-butene-1,4-diyl, 2-hexene-1,6-diyl, etc. "$C_{2-6}$ alkynyl" means a straight or branched carbon chain having at least one carbon-carbon triple bond, and from two to six carbon atoms; examples include ethynyl, propynyl, butynyl, and hexynyl.

The term "alkyl-$R^{25}$" includes optionally substituted alkyl groups such as methyl, ethyl, propyl, and butyl, attached to and $R^{25}$ group. $R^{25}$ generally includes hydrogen, alkenyl, hydroxy, thiol, alkoxy, thioalkoxy, amino, alkylamino, dialkylamino, aryl, heteroaryl, cyano, halo, sulfoxy, sulfonyl, —NHCOOH, —NHC(O)—, —NHSO$_2$—, —C(O)NH$_2$, heteroaryl or heterocycloalkyl groups such as morpholinyl or a group having the formula:

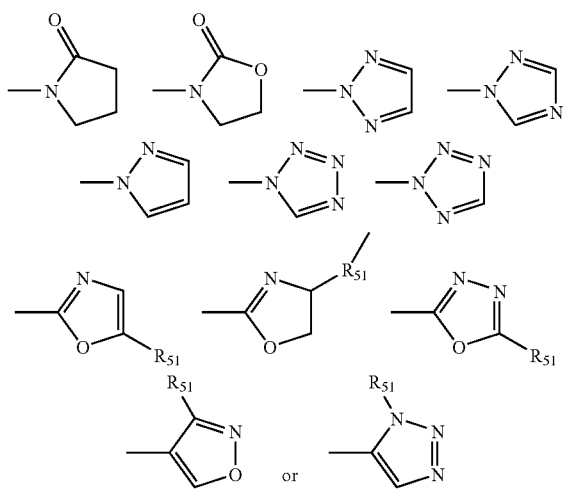

wherein $R_{51}$ is H or alkyl.

The terms "imidazole" and "imidazoline" herein alone or as part of another group includes substituted imidazoles and substituted imidazolines. Similarly, the term "tetrahydropyrimidine" includes substituted tetrahydropyrimidines. Likewise, the terms "piperazine", "piperidine" "morpholines", "homopiperazines", "homomorpholines" and "pyrrolidine" include substituted piperazines, substituted piperidines, substituted morpholines, substituted homomorpholines and substituted pyrrolidines, respectively Compounds of the present invention have the general formula I:

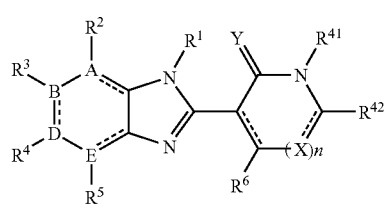

and include it enantiomers, diastereomers, pharmaceutically acceptable salts, hydrates, prodrugs and solvates thereof; wherein A, B, D, and E are each, independently, C or N;

X is selected from the group consisting of N or C wherein each of said N or C may be optionally substituted, independenty, with $R^7$ and n is 0, 1, 2, or 3;

Y is selected from the group consisting of O and S;

W is selected from the group consisting of N, C, O, and S, provided that when W is O or S, $R^{41}$ is absent;

$R^1$, $R^2$, $R^3$, $R^4$, $R^5$, $R^6$, $R^7$, $R^{41}$, and $R^{42}$ are each independently selected from the group consisting of H, $C_{1-6}$ alkyl, alkenyl, alkynyl, cycloalkyl, heterocycloalkyl, halo, amino, aminoalkyl, alkoxy, thioalkoxy, nitro, aryl, heteroaryl, alkoxyalkyl, thioalkoxyalkyl, aminoalkyl, aralkyl, heteroarylalkyl, heterocycloalkylalkyl, —CN, —CO$_2$R$^8$, —CONR$^9$R$^{10}$, —CO$_2$NR$^{11}$R$^{12}$, —NR$^{13}$CONR$^{14}$R$^{15}$, —NR$^{16}$SO$_2$R$^{17}$, —SO$_2$NR$^{18}$R$^{19}$, —C(NR$^{20}$)NR$^{21}$R$^{22}$, —NH-Z, —NH-Z-aryl, and NH-Z-heteroaryl, or any two of $R^2$ and $R^3$, $R^3$ and $R^4$, or $R^4$ and $R^5$ can be taken together to form a heterocyclic ring having at least one nitrogen atom;

Z is selected from the group consisting of $C_1$–$C_6$ alkyl, cycloalkyl, alkenyl, cycloalkenyl, and alkynyl; Z having one or more hydroxy, thiol, alkoxy, thioalkoxy, amino, halo, NR$^{23}$SO$_2$R$^{24}$ groups; Z optionally incorporating one or more groups selected from the group consisting of —CO, —CNOH, —CNOR$^{26}$, —CNNR$^{27}$, —CNNCOR$^{28}$ and —CNNSO$_2$R$^{29}$;

$R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, and $R^{26}$ are independently selected from the group consisting of H, alkyl, alkenyl, alkynyl, cycloalkyl, cycloalkylalkyl, hydroxy, alkoxy, aryl, heteroaryl, heterocyclyl, heteroarylalkyl, and alkyl-$R^{25}$ wherein $R^{25}$ is alkenyl, hydroxy, thiol, alkoxy, thioalkoxy, amino, alkylamino, dialkylamino, aryl, heteroaryl, cyano, halo, heteroaryl, heterocyloalkyl, sulfoxy, sulfonyl, —NR$^{27}$COOR$^{28}$, —NR$^{29}$C(O)R$^{30}$, —NR$^{31}$SO$_2$R$^{32}$, SO$_2$NR$^{31}$R$^{32}$, —C(O)NR$^{33}$R$^{34}$, and;

$R^{27}$, $R^{28}$, $R^{29}$, $R^{30}$, $R^{31}$, $R^{32}$, $R^{33}$ and $R^{34}$ are, independently, hydrogen, alkyl, or cycloalkyl.

In some embodiments of the present invention, if A, B, D and E are each C, then at least one of $R^2$ and $R^3$, $R^3$ and $R^4$ or $R^4$ and $R^5$ is taken together to form a heterocyclic ring. Preferred heterocyclic rings include optionally substituted imidazole, pyrazole, pyridine, pyrimidine, pyrrolidine, morpholine, piperidine, and piperazine.

In preferred embodiments, $R^3$ is an amino group such as NHCH$_2$CH$_2$OH, NMeCH$_2$CH$_2$OH, NEtCH$_2$CH$_2$OH, NHCH$_2$CH$_2$NH$_2$, NMeCH$_2$CH$_2$NH$_2$, NEtCH$_2$CH$_2$NH$_2$, NHCH$_2$CH$_2$NMe$_2$, NMeCH$_2$CH$_2$NMe$_2$, NEtCH$_2$CH$_2$NMe$_2$, NHCH$_2$CH$_2$NEt$_2$, NMeCH$_2$CH$_2$NEt$_2$, NEtCH$_2$CH$_2$NEt$_2$, NHCH$_2$CH$_2$N(CH$_2$CH$_2$)$_2$O, NMeCH$_2$CH$_2$N(CH$_2$CH$_2$)$_2$O, or NEtCH$_2$CH$_2$N(CH$_2$CH$_2$)$_2$O; a heteroaryl, a heterocyclo, or an alkoxy group, —OR, wherein R is H or alkyl-$R^{25}$ and $R^{25}$ is as defined above.

In some embodiments, $R^3$ is an optionally substituted piperidine. Preferred substituents are selected from the group consisting of hydroxy, thiol, amino, alkylamino, dialkylamino, alkoxy, thioalkoxy, 1,3 dioxolane (—OCHR)$_2$, 1,3 dioxane (—OCHRCHRCHRO—)—NHC(O)R, —NHCO$_2$R wherein R is alkyl or alkyl-$R^{25}$.

In some embodiments of the present invention, $R^3$ is an optionally substituted morpholine, homomorpholine, thiomorpholine, sulfoxymorpholine, or sulfonylmorpholine. Preferred substituents include hydroxy, thiol, amino, alkylamino, dialkylamino, alkoxy, thioalkoxy, alkyl-$R^{25}$, —NHC(O)R, —NHCO$_2$R, wherein R is hydrogen, alkyl or alkyl-$R^{25}$.

In some embodiments, $R^3$ is a pyrrolidine. Preferred pyrrolidines include, 3-hydroxylpyrrolidine, 3-alkoxy pyrrolidine, and 3-alkylamino pyrrolidine.

In some embodiments, $R^3$ is an optionally substituted N-tetrahydropyrimidine or N-imidazoline wherein the substituents are, preferably, alkyl, hydroxyalkyl, alkoxyalkyl, haloalkyl, cyanoalkyl, carboxyl, or carboxamide.

In some embodiments, $R^6$ is is selected from the group consisting of amino, NH-Z, NH-Z-aryl, and NH-Z-heteroaryl; wherein Z is defined as above.

In preferred embodiments, $R^6$ is selected from the group consisting H, 2-aminomethylpyridine, $NHCH_2CH(OH)aryl$, and $NHCH(CH_2OH)CH_2aryl$, wherein the aryl group is optionally substituted. In preferred embodiments, the aryl group is substituted with at least one Br, Cl, F, or methoxy and may have one of the following formulae:

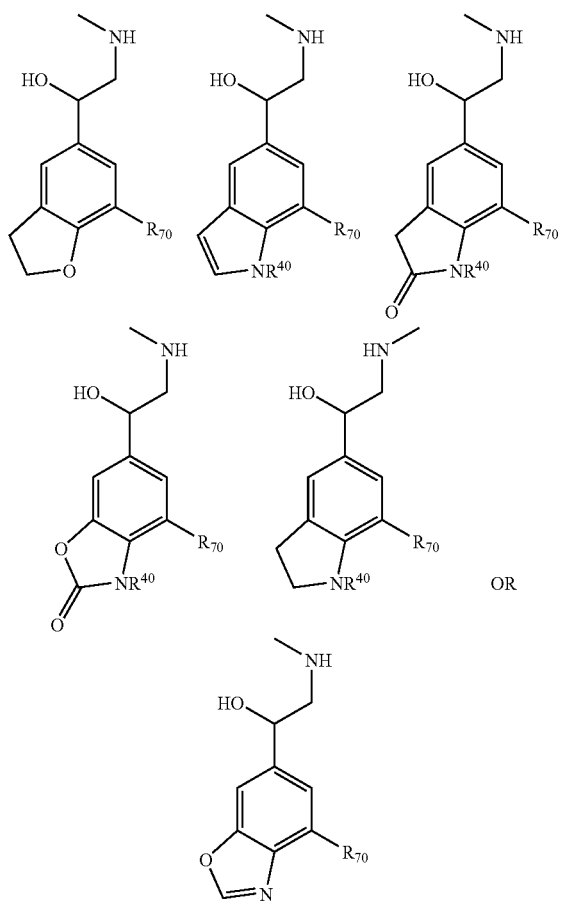

wherein $R^{40}$ is hydrogen or alkyl, preferably methyl, and $R^{70}$ is hydrogen or halogen, such as Br, Cl or F.

Suitable examples of salts of the compounds according to the invention include inorganic or organic acids. These include, but are not limited to, hydrochloride, hydrobromide, sulfate, methanesulfonate, maleate, fumarate, phosphate and other pharmaceutically acceptable salts. Salts which are unsuitable for pharmaceutical uses but which can be employed, for example, for the isolation or purification of free compounds of formula I or their pharmaceutically acceptable salts, are also included.

All stereoisomers of the compounds of the instant invention are contemplated, either in admixture or in pure or substantially pure form. The definition of the compounds according to the invention embraces all possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates by conventional methods, such as, for example, salt formation with an optically active acid followed by crystallization.

It should be understood that the present invention includes prodrug forms of the compounds of formula I. Various forms of prodrugs are well known in the art. For examples of such prodrug derivatives, see:
(a) Design of Prodrugs, edited by H. Bundgaard (Elsevier, 1985); and Methods in Enzymology, Vol. 42, pp. 309–396, edited by K. Widder et al., (Academic Press, 1985);
(b) A Textbook of Drug Design and Development, edited by Krosgaard-Larsen and H. Bundgaard, Chapter 5, "Design and Application of Prodrugs," by H. Bundgaard, pp. 113–191 (1991);
(c) H. Bundgaard, Advanced Drug Deliver Reviews, 8, pp. 1–38 (1992);
(d) H. Bundgaard et al., Journal of Pharmaceutical Sciences, 77, 285 (1988); and
(e) N. Kayeka et al., Chem. Phar. Bull., 32, 692 (1984).

The invention also provides a pharmaceutical composition comprising a compound of formula I, as defined above, and a pharmaceutically acceptable carrier and at least one other anti-cancer agent formulated as a fixed dose. Preferred anti-cancer agents are selected from the group consisting of: tamoxifen, toremifen, raloxifene, droloxifene, iodoxyfene, megestrol acetate, anastrozole, letrazole, borazole, exemestane, flutamide, nilutamide, bicalutamide, cyproterone acetate, goserelin acetate, luprolide, finasteride, HERCEPTIN(trastuzumab), methotrexate, 5-fluorouracil, cytosine arabinoside, doxorubicin, daunomycin, epirubicin, idarubicin, mitomycin-C, dactinomycin, mithramycin, cisplatin, carboplatin, melphalan, chlorambucil, busulphan, cyclophosphamide, ifosfamide, nitrosoureas, thiotephan, vincristine, TAXOL(paclitaxel), TAXOTERE(docetaxel), etoposide, teniposide, amsacrine, Irinotecan, topotecan, an epothilone; a tyrosine kinase inhibitor such as IRESSA (gefitinib) or TARCEVA(erlotinib); an angiogenesis inhibitor; an EGF inhibitor; a VEGF inhibitor; a CDK inhibitor; a Her1/2 inhibitor and monoclonal antibodies directed against growth factor receptors such as erbitux (EGF) and HERCEPTIN(trastuzumab) (Her2).

The invention further provides a method of treating a condition via modulation of at least one tyrosine kinase enzyme comprising administering to a mammalian species in need of such treatment an effective amount of a compound of formula I, as defined above.

Additionally, the invention provides a method of treating a condition via modulation of at least one tyrosine kinase enzyme comprising administering to a mammalian species in need of such treatment an effective amount of a compound of formula I, as defined above, in combination (simultaneously or sequentially) with at least one other anti-cancer agent.

A preferred condition, treated by said methods of the instant invention, is cancer. Additionally, the tyrosine kinase enzyme may include (but is not limited to): Abl, CDK's, EGF, EMT, FGF, FAK, Flk-1/KDR, HER-2, IGF-1R, IR, LCK, MEK, MET, PDGF, Src, and VEGF.

The invention also provides a method for treating cancer, comprising administering to a mammalian species in need of such treatment, a therapeutically effective amount of at least one of the pharmaceutical compositions defined above.

The invention further provides a method for treating proliferative diseases, comprising administering to a mammalian species in need of such treatment a therapeutically effective amount of at least one of the pharmaceutical compositions defined above.

Certain compounds of formula I may generally be prepared according to the following schemes and the knowledge of one skilled in the art. Solvates (e.g., hydrates) of the compounds of formula I are also within the scope of the present invention. Methods of solvation are generally known in the art. Accordingly, the compounds of the instant invention may be in the free or hydrate form, and may be obtained by methods exemplified by the following schemes below.

Schemes I-IX illustrate the preparation of compounds claimed in this invention. The examples, which follow, illustrate the compounds that can be synthesized by these schemes. The schemes are not limited by the examples listed or by any substituents employed for illustrative purposes.

Scheme I describes the preparation of the benzimidazoles. The starting diamines 1 are readily available using literature methods or are obtained commercially. The diamine is then condensed with an aldehyde 2 to provide the benzimidazole 3. Further modification of the functional groups appended to A-E, or $R^7$, $R^{41}$, or $R^{42}$ are then possible.

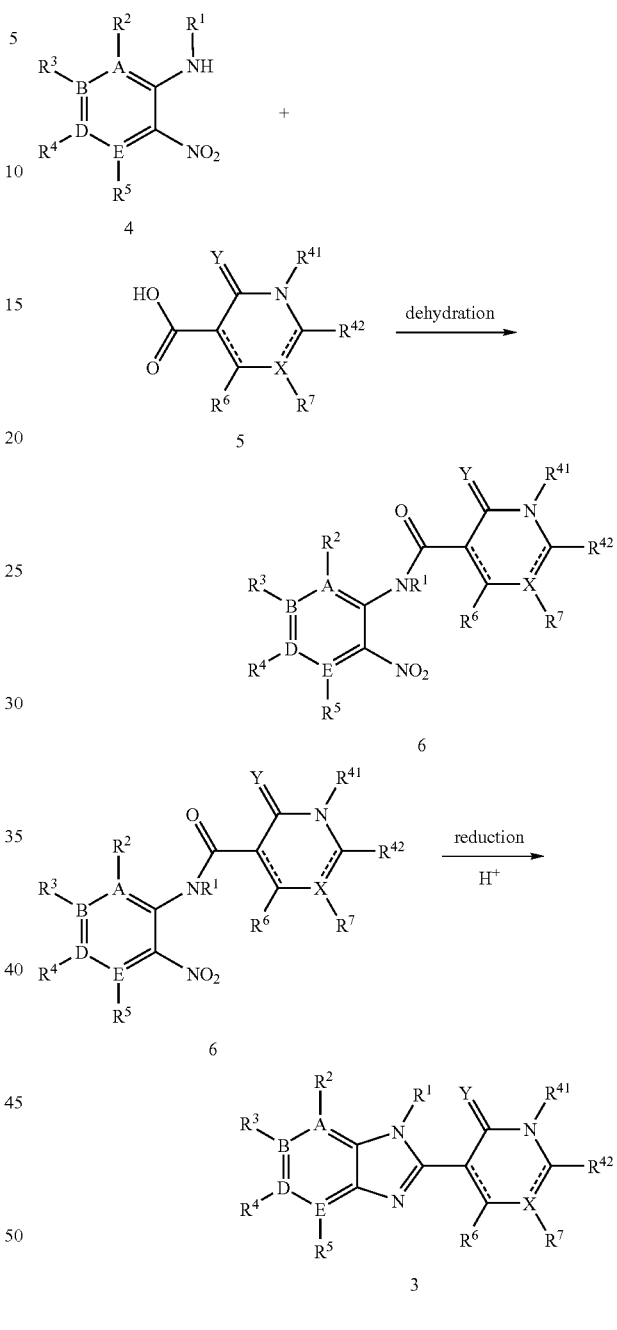

Alternatively, the benzimidazole could be formed in a step-wise manner (see Scheme II and Scheme III). Scheme II describes the preparation of the benzimidazoles via the amide formation using the acid chloride of 5 or any of the commonly used peptide coupling reagents such as DCC (dicyclohexylcarbodiimide), EDCI (1-(3-dimethylaminopropyl)-3-ethylcarbodiimide hydrochloride), etc. Once the amide 6 is formed the nitro group is reduced using catalytic hydrogenation, transfer hydrogenation or chemical reduction such as $SnCl_2$ or iron powder or other methods known in the art for reduction of aryl nitro groups. Treatment of the aniline with acid then forms the benzimidazole.

Alternatively, the diamine 1 could be used in the amide forming reaction. Such a diamine could be deprotonated with strong base such as LiHMDS or LDA followed by addition of the alkyl ester derivative of the said acid 5, preferably the methyl ester, to provide an intermediate which could be dehydrated preferably with $POCl_3$ to provide the benzimidazole 3

Scheme III illustrates the condensation of the diamine 1 with an aldehyde 2 to give the imine 7. Once the Schiff base 7 is formed the arylimine is induced to undergo oxidative cyclization using iodobenzene diacetate (IDB) as an oxidant to provide the benzimidazole.

Scheme III

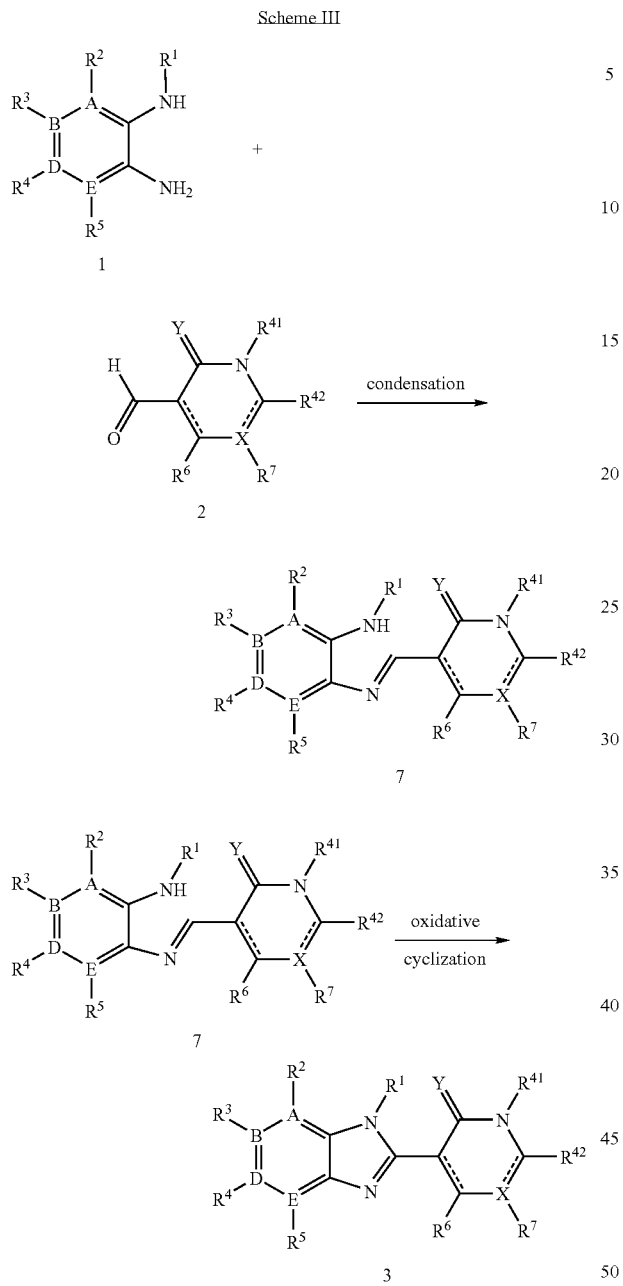

Scheme IV

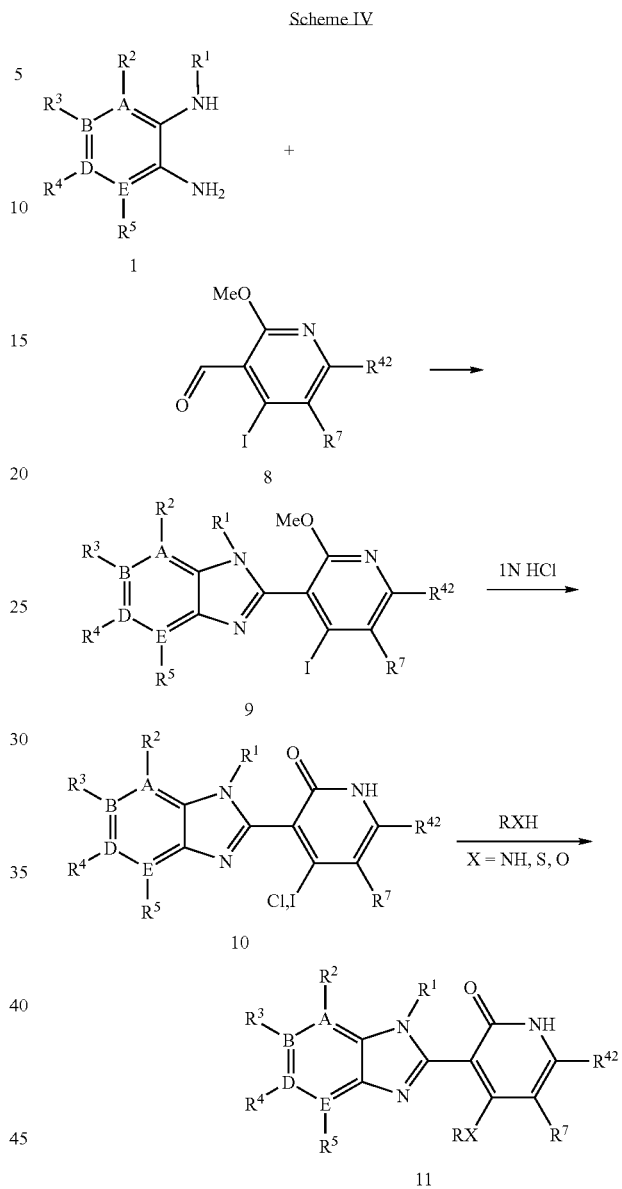

For example, Scheme IV illustrates the use of 4-iodo-2-methoxy-pyridine-3-carbaldehyde 8 to provide the functionalized benzimidazole 9. Hydrolysis of the methoxy group using protic acid conditions, TMSI (trimethylsilyl iodide), BBr$_3$, or other conditions known in the art for cleaving a methyl ether provides the halopyridone 10. For some benzimidazoles where A, B, D or E is "N" hydroxylsis of the methoxy group results in cleavage of the benzimidazole ring to an amino amide. This amide can be reclosed with POCl$_3$ or other dehydrating reagent to reclose the benzimidazole ring and provide halopyridone 9. Addition of heteroatom nucleophiles using amines, alcohols or thiols then provides the substituted pyridones 11. Other functionality could be incorporated into the aldehyde and the above example is included for illustrative purposes only.

Likewise the aryl ring of the benzimidazole prepared using Schemes I, II or III can be modified. For example introduction of a cyano group for R$^3$ on the benzimidazole allows for the formation of heterocycles such as imidazole, imidazolines, oxazolines, thiazolines, amides, or amidines. Scheme V illustrates such transformations. Starting from the cyano-substituted benzimidazole 12 the heterocycle can be modified as illustrated in Scheme V to provide 13. Imidate formation preferably using ethanol and acid provides intermediate 14. Imidate 14 can be transformed using diamines to form imidazolines, amino alcohols to form oxazolines, amino acetals to form imidazoles, and amino thiols to form thiazolines 15. Alternatively the imidate can be hydrolyzed to the acid and coupled with amines using any of the standard amide formation reagents (DCC, EDCI, etc.) to form amides 16. Imidate 14 is also a useful intermediate for the preparation of amidines 17 by reacting with amines.

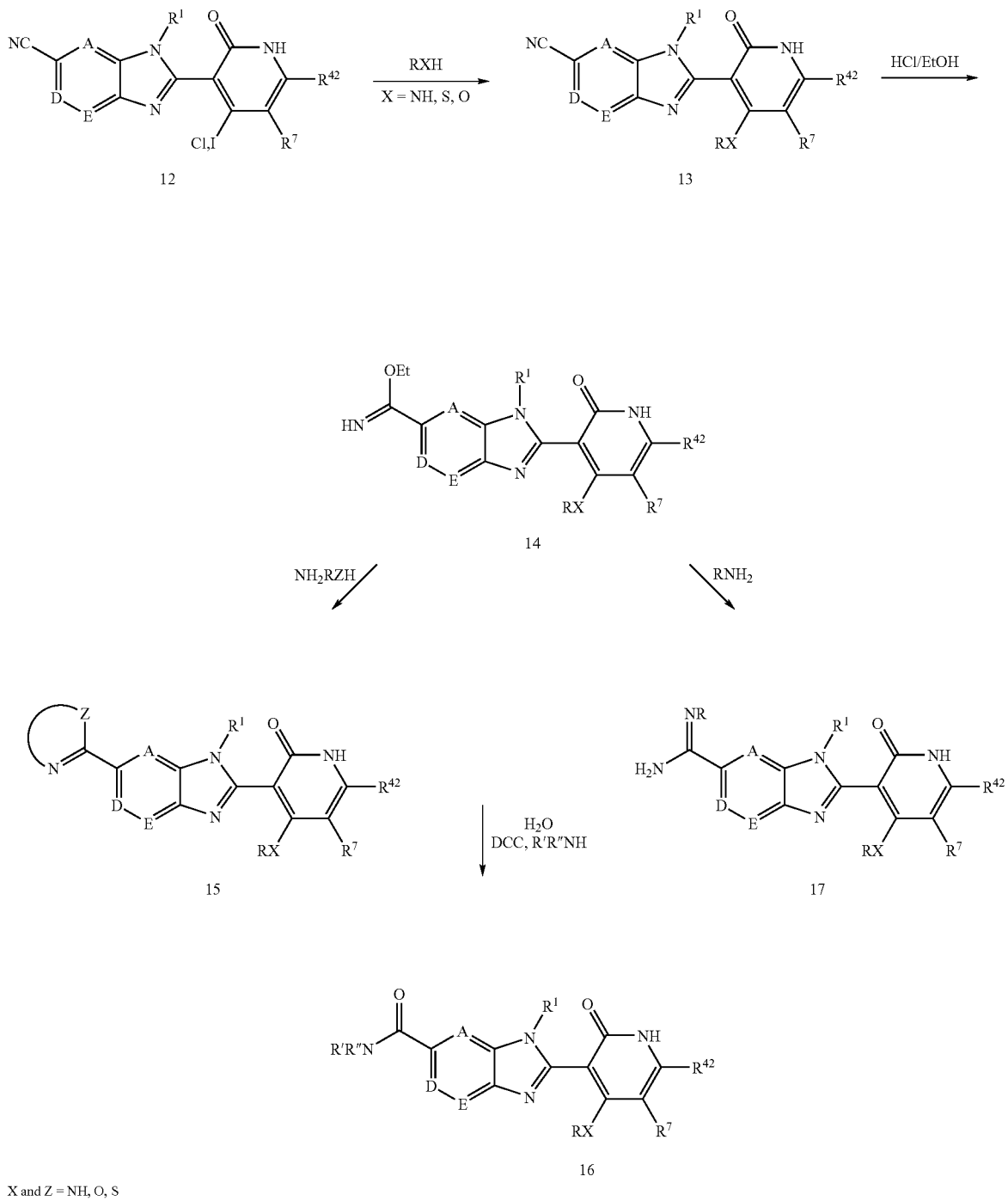

Scheme V

Scheme VI illustrates further transformation of benzimidazoles that bear a halogen atom using palladium catalysis using conditions developed by Suzuki [Yang et al. *Acta Chem. Scand.* (1993) 221; Suzuki et al. *Synth. Commun.* (1981) 11: 513] or Buchwald/Hartwig [Buchwald et al. *J. Am. Chem. Soc.* (1994) 116: 7901; Hartwig et al. *J. Am. Chem. Soc.* (1994) 116: 5969; Hartwig. *Angew. Chem., Int. Ed. Engl.* (1998) 37: 2046] and variations of these methods. Preparation of a bromide substituted benzimidazole 18 is envisioned to provide a substrate for Suzuki coupling with aryl, vinyl, and heterocyclic boronic acids to provide benzimidazoles 19. Likewise, amines and heterocycles such as piperazine or morpholine derivatives 20 can be prepared from the same bromide using amines under conditions described by Buchwald and Hartwig or variations thereof.

Scheme VI

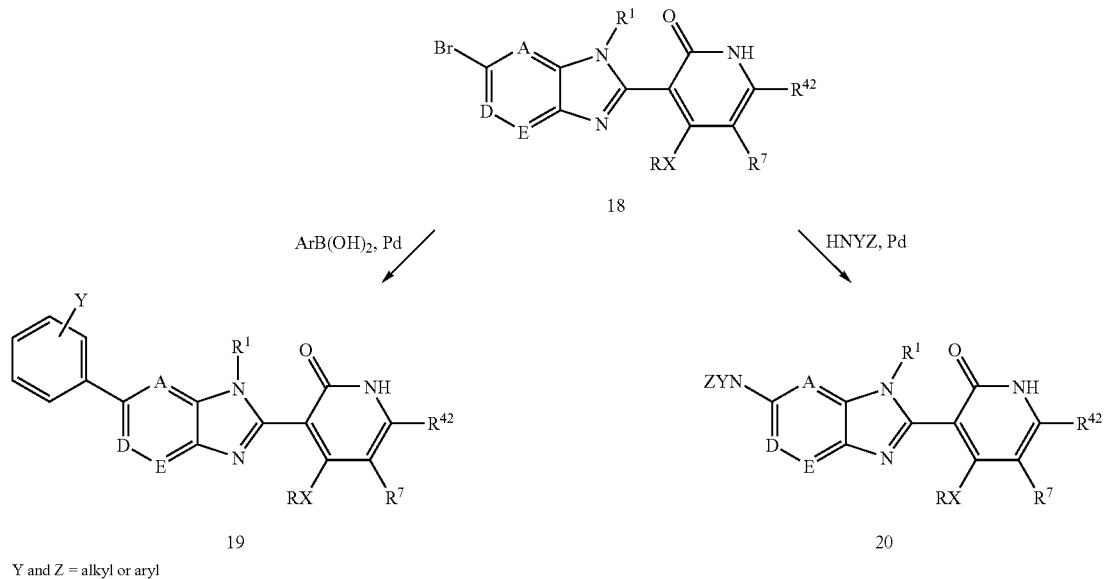

Y and Z = alkyl or aryl
X = NH, O, S

Alternatively amine and heterocyclic derivatives such as 20 is prepared using intermediate 6 described in Scheme II. When the $R^3$ of 6 is a halogen, preferably F, the halogen can be displaced with amines, alcohols, heterocyclic amines and other nitrogen containing heterocycles such as piperazine, piperidine, 4-amino piperidine, morpholine, imidazole, etc (Scheme VII). The terminal nitrogen of piperazine or 4-amino piperidine is then alkylated using standard alkylation conditions or reacted with aldehydes in a reductive amination reaction to provide alkylated derivatives. Alternatively the terminal nitrogen atom of piperazine or 4-amino piperidine can be acylated or carbamoylated using any number of conditions that are routine for someone skilled in the art of organic synthesis. Following the example illustrated in Scheme II compounds such as 20 could be prepared.

Scheme VII

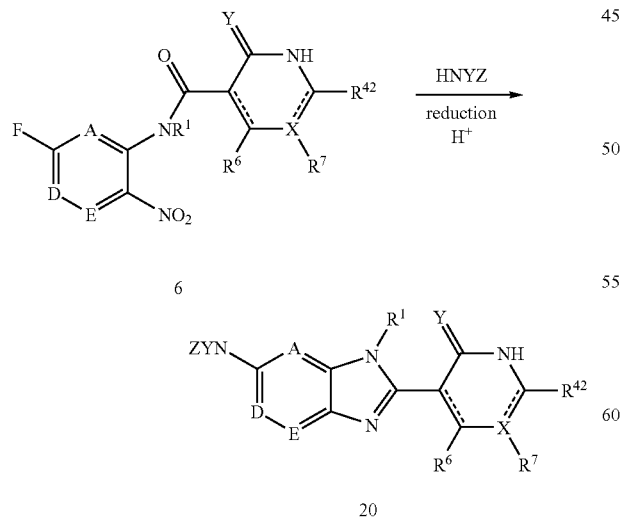

Alternatively amines, heterocycles, and alcohols can be introduced at $R^3$ using a nucleophilic aromatic substitution reaction started from an intermediate 21 were $R^3$ is halogen, preferably Cl. The halogen can be activated by either A and/or D being a N, or by being activated by a p-nitro group ($NR^1_2$; where $R^1$ is O). The halogen can be displaced with amines, alcohols, heterocyclic amines and other nitrogen containing heterocycles such as piperazine, piperidine, 4-amino piperidine, morpholine, imidazole, etc (Scheme VIII). The $R^1 2$ and $NR^2 2$ can then be deprotected or reduced (when $R^1$ or $R^2$ is O) to provide the diamine. The terminal nitrogen of piperazine or 4-amino piperidine is then alkylated using standard alkylation conditions or reacted with aldehydes in a reductive amination reaction to provide alkylated derivatives. Alternatively the terminal nitrogen atom of piperazine or 4-amino piperidine is acylated or carbamoylated using any number of conditions that are routine for someone skilled in the art of organic synthesis. The resulting nitro or amino groups $NR^1_2$ and $NR^2_2$ are then deprotected or reduced (when $R^1$ or $R^2$ is O) to provide the diamine 22 and processed as illustrated in Scheme III.

Scheme VIII

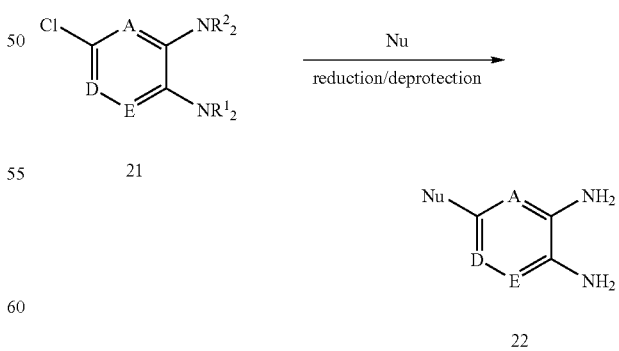

Scheme IX illustrates the synthesis of a specific heterocylic benzimidazole for illustration. Starting from 2,6-dichloro-3-nitro-pyridin-4-ylamine, 23 (R. J. Rousseau and R. K. Robins *J. Heterocyclic Chem.* 2 (1965), p.196) a methyl group is introduced using Pd catalysis and trimethylaluminium to provide pyridine 24. The chloro group of 24 can be displaced by any number of nucleophiles but amine nucleophiles are specfically envisioned such as morpholine, piperazine, piperadine and pyrolidine and substituted derivatives thereof. The resulting nitro aniline 25 can be reduced by catalytic hydrogenation, transfer hydrogenation or chemical reduction such as $SnCl_2$ or iron powder or other methods known in the art for reduction of aryl nitro groups. The diamine can be 1' can be isolated or condensed crude with aldehyde 8 as illustrated in Scheme IV. Following Scheme IV benzimidazole derivatives such as 11' can be prepared.

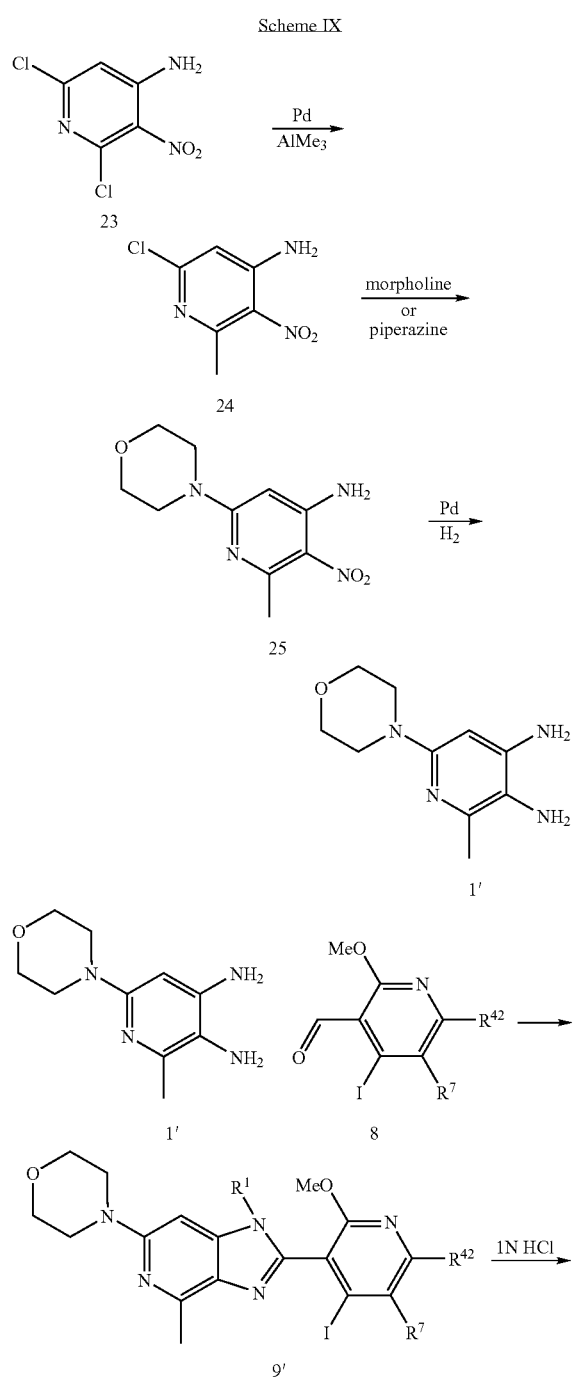

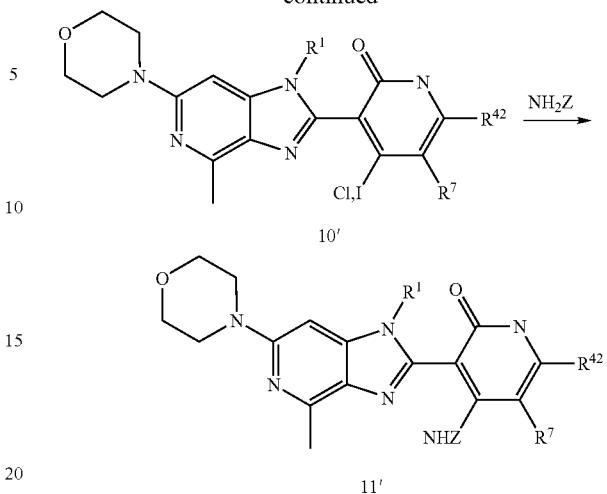

Utility

The compounds according to the invention have pharmacological properties; in particular, the compounds of formula I are tyrosine kinase enzyme inhibitors. The novel compounds of formula I are thus useful in the therapy of a variety of proliferative diseases (including but not limited to diseases associated with tyrosine kinase enzymes) such as cancer, autoimmune diseases, viral diseases, fungal diseases, neurodegenerative disorders and cardiovascular disease.

More specifically, the compounds of formula I are useful in the treatment of a variety of cancers, including, but not limited to, the following:

a) carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

b) hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkett's lymphoma;

c) hematopoietic tumors of myeloid lineage, including acute and chronic myelogenous leukemias, myelodysplastic syndrome and promyelocytic leukemia;

d) tumors of mesenchymal origin, including fibrosarcoma and rhabdomyosarcoma;

e) tumors of the central and peripheral nervous system, including astrocytoma, neuroblastoma, glioma and schwannomas; and f) other tumors, including sarcoma, melanoma, seminoma, teratocarcinoma, osteosarcoma, xenoderoma pigmentosum, keratoctanthoma, thyroid follicular cancer and Kaposi's sarcoma.

Due to the key role of tyrosine kinases in the regulation of cellular proliferation in general, inhibitors could act as reversible cytostatic agents which may be useful in the treatment of any disease process which features abnormal cellular proliferation, e.g., benign prostatic hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of formula I may induce apoptosis. The apoptotic response is aberrant in a variety of human diseases. Compounds of formula I, as modulators of apoptosis, will be useful in the treatment of cancer (including but not limited to those types mentioned herein above), viral infections (including but not limited to herpesvirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of formula I may modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

Compounds of formula I may also be useful in the chemoprevention of cancer. Chemoprevention is defined as inhibiting the development of invasive cancer by either blocking the initiating mutagenic event or by blocking the progression of premalignant cells that have already suffered an insult or inhibiting tumor relapse.

Compounds of formula I may also be useful in inhibiting tumor angiogenesis and metastasis.

The compounds of this invention may also be useful in combination (administered together or sequentially) with known anti-cancer treatments such as radiation therapy or with cytostatic or cytotoxic agents, such as for example, but not limited to, DNA interactive agents, such as cisplatin or doxorubicin; topoisomerase II inhibitors, such as etoposide; topoisomerase I inhibitors such as Irinotecan or topotecan; tubulin interacting agents, such as paclitaxel, docetaxel or the epothilones; hormonal agents, such as tamoxifen; thymidilate synthase inhibitors, such as 5-fluorouracil; and anti-metabolites, such as methotrexate; tyrosine kinase inhibitors such as IRESSA(gefitinib) and TARCEVA(erlotinib); angiogenesis inhibitors; EGF inhibitors; VEGF inhibitors; CDK inhibitors; Her1/2 inhibitors and monoclonal antibodies directed against growth factor receptors such as erbitux (EGF) and HERCEPTIN(trastuzumab) (Her2).

If formulated as a fixed dose, such combination products employ the compounds of this invention within the dosage range described below and the other pharmaceutically active agent or treatment within its approved dosage range. Compounds of formula I may also be administered sequentially with known anticancer or cytotoxic agents when a combination formulation is inappropriate. The invention is not limited in the sequence of administration; compounds of formula I may be administered either prior to or after administration of the known anticancer or cytotoxic agent(s).

Further subject matter of the invention also includes pharmaceuticals for use, as described above, including controlling cancer, inflammation and arthritis, which contain at least one compound of the formula I as defined above or at least one of its pharmacologically acceptable acid addition salts, and the use of a compound of the formula I as defined above for the preparation of a pharmaceutical having activity against proliferative diseases as described previously including against cancer, inflammation and/or arthritis.

The pharmacological properties of the compounds of this invention may be confirmed by a number of pharmacological assays. The exemplified pharmacological assays which follow have been carried out with the compounds according to the invention and their salts.

Biological Assays

A. CDK 2/Cyclin E Kinase Assay

Kinase reactions consisted of 5 ng of baculovirus expressed GST-CDK2/cyclin E complex, 0.5 µg GST-RB fusion protein (amino acids 776–928 of retinoblastoma protein), 0.2 µCi $^{33}$P γ-ATP, 25 µM ATP in 50 µl kinase buffer (50 mM Hepes, pH 8.0, 10 mM MgCl$_2$, 1 mM EGTA, 2 mM DTT). Reactions were incubated for 45 minutes at 30° C. and stopped by the addition of cold trichloroacetic acid (TCA) to a final concentration of 15%. TCA precipitates were collected onto GF/C unifilter plates (Packard Instrument Co., Meriden, Conn.) using a Filtermate universal harvester (Packard Instrument Co., Meriden, Conn.) and the filters were quantitated using a TopCount 96-well liquid scintillation counter (Packard Instrument Co., Meriden, Conn.). Dose response curves were generated to determine the concentration required inhibiting 50% of kinase activity ($IC_{50}$). Compounds were dissolved at 10 mM in dimethylsulfoxide (DMSO) and evaluated at six concentrations, each in triplicate. The final concentration of DMSO in the assay equaled 2%. $IC_{50}$ values were derived by non-linear regression analysis and have a coefficient of variance (SD/mean, n=6)=14%.

B. EMT Kinase Assay

A filter-based kinase assay, measuring the phosphorylation of Gst-SLP76 by Gst-Emtk, was employed to determine the compound inhibitory activity against Emt. The kinase reaction was performed in a 96-well plate at room temperature for 15 min before being terminated by adding 100 µl of 20% trichloroacetic acid (TCA) containing 0.1 M sodium pyrophosphate. The kinase reaction mixture (60 µl) contained 25 mM HEPES, pH 7.0, 0.1 mg/ml BSA, 5 mM MgCl$_2$, 5 mM MnCl$_2$, 8 ng of enzyme (Gst-Emtk), 5 µg of the substrate protein (Gst-SLP76), 1 µM ATP, 0.4 µCi of [γ-P$^{33}$]ATP and the tested compound (at various concentrations). After termination, the proteins were allowed to precipitate in the presence of TCA for 1 hr at 4° C. The precipitated proteins were then harvested on a filter plate (UniFilter-96, GF/C, Packard Instrument) and washed to remove excess [γ-P$^{33}$]ATP. The radioactivity was determined using a TopCount NXT (Packard Instrument) after adding 35 µl of Microscint 20 (Packard Instrument).

C. FAK Tyrosine Kinase Assay

The Focal Adhesion kinase was assayed using the synthetic polymer poly(Glu/Tyr) (Sigma Chemicals) as a phosphoacceptor substrate. Each reaction mixture consisted of a total volume of 50 ul and contained 100 ng of baculovirus-expressed enzyme, 2 µg of poly(Glu/Tyr), 1 µM of ATP, and 0.2 µCi of [γ-$^{33}$P]ATP. The mixtures also contained 40 mM Tris.HCl, pH 7.4, 1 mM MnCl$_2$, 0.5 mM DTT, and 0.1 mg/ml bovine serum albumin. The reaction mixtures were incubated at 26° C. for 1 hour and kinase activity was determined by quantitation of the amount of radioactive phosphate transferred to the poly(Glu/Tyr) substrate. Incorporation was measured by the addition of cold trichloroacetic acid (TCA) precipitation of the proteins which were collected onto GF/C unifilter plates (Packard Instrument Co., Meriden, Conn.) using a Filtermate universal harvester and the filters were quantitated using a TopCount 96-well liquid scintillation counter (Packard Instrument Co., Meriden, Conn.). Compounds were dissolved in dimethyl sulfoxide to a concentration of 10 mM and were evaluated at six concentrations, each in triplicate. The final concentration of DMSO added to the kinase assays was 0.5%, which has been shown to have no effect on kinase activity. IC50 values were derived non-linear regression analysis and have a coefficient of variance (SD/mean, n=6)=16%.

D. HER-1/HER-2 Kinase Assay

Kinase reactions consisted of 10 ng of baculovirus expressed GST-HER1, 100 ng of HER2, 100 ng/ml poly (Glu/Tyr) (Sigma), 0.2 µCi 33P γ-ATP, 1 µM ATP in 50 µl kinase buffer (50 mM Tris, pH 7.5, 10 mM MnCl$_2$, 0.5 mM DTT). Reactions were incubated for 1 h at 27 C and stopped by the addition of cold trichloroacetic acid (TCA) to a final concentration 15%. TCA precipitates were collected onto GF/C unifilter plates (Packard Instrument Co., Meriden, Conn.) using a Filtermate universal harvester (Packard Instrument Co., Meriden, Conn.) and the filters were quantitated using a TopCount 96-well liquid scintillation counter (Packard Instrument Co., Meriden, Conn.). Dose response curves were generated to determine the concentration required to inhibit 50% of kinase activity (IC$_{50}$). Compounds were dissolved at 10 mM in dimethylsulfoxide (DMSO) and evaluated at six concentrations, each in triplicate. The final concentration of DMSO in the assay equaled 1%. IC$_{50}$ values were derived by non-linear regression analysis and have a coefficient of variance (SD/mean, n=6) =16%.

E. IGF-Receptor Tyrosine Kinase Assay

The IGF-1 receptor tyrosine kinase was assayed using the synthetic polymer poly(Glu/Tyr) (Sigma Chemicals) as a phosphoacceptor substrate. Each reaction mixture consisted of a total volume of 50 ul and contained 125 ng of baculovirus expressed enzyme, 2.5 µg of poly(Glu/Tyr), 25 µM of ATP, and 0.1 µCi of [γ-$^{33}$P]ATP. The mixtures also contained 20 mM MOPS, pH 7.0, 5 mM MnCl$_2$, 0.5 mM DDT, and 0.1 mg/ml bovine serum albumin. The reaction mixtures were incubated at 30° C. for 45 minutes and kinase activity was determined by quantitation of the amount of radioactive phosphate transferred to the poly(Glu/Tyr) substrate. Incorporation was measured by the addition of cold trichloroacetic acid (TCA) precipitation of the proteins which were collected onto GF/C unifilter plates (Packard Instrument Co., Meriden, Conn.) using a Filtermate universal harvester and the filters were quantitated using a TopCount 96-well liquid scintillation counter (Packard Instrument Co., Meriden, Conn.). Compounds were dissolved in dimethyl sulfoxide to a concentration of 10 mM and were evaluated at six concentrations, each in triplicate. The final concentration of DMSO added to the kinase assays was 0.5%, which has been shown to have no effect on kinase activity. IC50 values were derived by non-linear regression analysis and have a coefficient of variance (SD/mean, n=6) =16%.

F. Insulin Receptor Tyrosine Kinase Assay

The Insulin Receptor Tryrosine kinase was assayed using the synthetic polymer poly(Glu/Tyr) (Sigma Chemicals) as a phosphoacceptor substrate. Each reaction mixture consisted of a total volume of 50 ul and contained 90 ng of baculovirus-expressed enzyme, 2.5 µg of poly(Glu/Tyr), 25 µM of ATP, and 0.1 µCi of [γ-$^{33}$P]ATP. The mixtures contained also 20 mM Tris.HCl, pH 7.4, 5 mM MnCl$_2$, 0.5 mM DTT, and 0.1 mg/ml bovine serum. The reaction mixtures were incubated at 26° C. for 1 hour and kinase activity was determined by quantitation of the amount of radioactive phosphate transferred to the poly(Glu/Tyr) substrate. Incorporation was measured by the addition of cold trichloroacetic acid (TCA) precipitation of the proteins which were collected onto GF/C unifilter plates (Packard Instrument Co., Meriden, Conn.) using a Filtermate universal harvester and the filters were quantitated using a TopCount 96-well liquid scintillation counter (Packard Instrument Co., Meriden, Conn.). Compounds were dissolved in dimethyl sulfoxide to a concentration of 10 mM and were evaluated at six concentrations, each in triplicate. The final concentration of DMSO added to the kinase assays was 0.5%, which has been shown to have no effect on kinase activity. IC50 values were derived non-linear regression analysis and have a coefficient of variance (SD/mean, n=6) =16%.

G. LCK Kinase Assay

Kinase reactions consisted of 10 ng of baculovirus expressed 10 ng GST-Lck, 100 ng/ml poly(Glu/Tyr) (Sigma), 0.2 µCi 33P γ-ATP, 1 µM ATP in 50 µl kinase buffer (50 mM Tris, pH 7.5, 10 mM MnCl2, 0.5 mM DTT). Reactions were incubated for 1 h at 27 C and stopped by the addition of cold trichloroacetic acid (TCA) to a final concentration 15%. TCA precipitates were collected onto GF/C unifilter plates (Packard Instrument Co., Meriden, Conn.) using a Filtermate universal harvester (Packard Instrument Co., Meriden, Conn.) and the filters were quantitated using a TopCount 96-well liquid scintillation counter (Packard Instrument Co., Meriden, Conn.). Dose response curves were generated to determine the concentration required to inhibit 50% of kinase activity (IC$_{50}$). Compounds were dissolved at 10 mM in dimethylsulfoxide (DMSO) and evaluated at six concentrations, each in triplicate. The final concentration of DMSO in the assay equaled 1%. IC$_{50}$ values were derived by non-linear regression analysis and have a coefficient of variance (SD/mean, n=6)=16%.

H. MET Kinase Assay

Kinase reactions consisted of 10 ng of baculovirus expressed GST-Met, 2.5 ug poly(Glu/Tyr) (Sigma), 0.2 µCi 33P γ-ATP, 10 µM ATP in 50 µl kinase buffer (40 mM Tris, pH 7.5, 1 mM MnCl2, 0.50 mM DTT). Reactions were incubated for 1 h at 27 C and stopped by the addition of cold trichloroacetic acid (TCA) to a final concentration 3.5%. TCA precipitates were collected onto GF/C unifilter plates (Packard Instrument Co., Meriden, Conn.) using a Filtermate universal harvester (Packard Instrument Co., Meriden, Conn.) and the filters were quantitated using a TopCount 96-well liquid scintillation counter (Packard Instrument Co., Meriden, Conn.). Dose response curves were generated to determine the concentration required to inhibit 50% of kinase activity (IC$_{50}$). Compounds were dissolved at 10 mM in dimethylsulfoxide (DMSO) and evaluated at seven concentrations, each in triplicate. The final concentration of DMSO in the assay equaled 1%. IC$_{50}$ values were derived by non-linear regression analysis and have a coefficient of variance (SD/mean, n=6)=16%.

I. PDGF Receptor Kinase Assay

Kinase reactions consisted of 70 ng of baculovirus expressed GST-PDGFbR, 0.3 ug biotinylated poly(Glu/Tyr)

(Sigma), in 50 µl kinase buffer (20 mM Hepes, pH 7.5, 0.7 uM ATP, 10 mM MnCl2, 0.5 mM DTT, 0.5 mM NaCl, 0.1 mg/ml BSA). Reactions were incubated for 30 minutes at room temperature with shaking and stopped by the addition of 10 ul of 0.2M EDTA, pH 8.0. 150 ul of HTRF detection buffer was added and incubated for 1 hour and 30 minutes at room temperature. Counts were quantitated on Discovery HTRF Packard Instrument.

J. VEGFR-2 (KDR) Kinase Assay

Kinase reactions consisted of 7.5 ng of baculovirus expressed GST-KDR, 1.5 ug poly(Glu/Tyr) (Sigma), 0.04 µCi 33P γ-ATP, 2.5 µM ATP in 50 µl kinase buffer (25 mM Tris, pH 7.5, 1.8 mM MnCl2, 0.0.625 mM DTT). Reactions were incubated for 1 h at 27 C and stopped by the addition of cold trichloroacetic acid (TCA) to a final concentration 15%. TCA precipitates were collected onto GF/C unifilter plates (Packard Instrument Co., Meriden, Conn.) using a Filtermate universal harvester (Packard Instrument Co., Meriden, Conn.) and the filters were quantitated using a TopCount 96-well liquid scintillation counter (Packard Instrument Co., Meriden, Conn.). Dose response curves were generated to determine the concentration required to inhibit 50% of kinase activity ($IC_{50}$). Compounds were dissolved at 10 mM in dimethylsulfoxide (DMSO) and evaluated at six concentrations, each in triplicate. The final concentration of DMSO in the assay equaled 1%. $IC_{50}$ values were derived by non-linear regression analysis and have a coefficient of variance (SD/mean, n=6)=16%.

K. Cytotoxicity Assay (HT-29–Colon, Colo205, MCF-7-Breast)

Tumor cell lines are maintained in McCoy's 5A medium (GIBCO) and 10% heat inactivated fetal bovine serum (GIBCO). The in vitro cytotoxicity is assessed in tumor cells by a tetrazolium-based colorimetric assay which takes advantage of the metabolic conversion of MTS (3-(4,5-dimethylthiazol-2-yl)-5-(3-carboxymethoxyphenyl)-2-(4-sulphenyl)-2H-tetrazolium, inner salt) (Promega) to a reduced form that absorbs light at 492 nm (1). Cells are seeded 24 hr prior to drug addition. Following a 72 hour incubation at 37° C. with serially diluted test compound, MTS (Riss, T. L, et al., Comparison of MTT, XTT, and a novel tetrazolium compound MTS for in vitro proliferation and chemosensitivity assays," *Mol. Biol. Cell* 3 (Suppl.): 184a, 1992), in combination with the electron coupling agent phenazine methosulfate, is added to the cells. The incubation is continued for 3 hours, then the absorbency of the medium at 492 nm is measured with a spectrophotometer to obtain the number of surviving cells relative to control populations. The results are expressed as median cytotoxic concentrations ($IC_{50}$ values).

Biological Activity; the compounds of the present invention had kinase activity of <25 uM against one or more of the following kinases CDK, EMT, FAK, Her1, Her2, IGF, IR, LCK, MET, PDGF, VEGF.

General Procedure for the Preparation of 2-Hydroxy-2-(substituted-phenyl)-ethylamines:

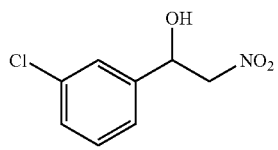

1-(3–Chloro-phenyl)-2-nitro-ethanol: To a solution of 3-chloro-benzaldehyde (20 g, 0.142 mol) in nitromethane (100 mL) were added magnesium sulfate (37.6 g, 0.312 mol) and phosphazene base $P_1$-t-bu-tris(tetramethylene) (4.43 g, 0.014 mol). The reaction mixture was stirred at room temperature for 2 h. After concentration in vacuo, the residue was purified by flash chromatography (25% EtOAc/hexane) to yield the title compound (26.4 g, 100%) as a green-yellow oil. $^1$H NMR (300 MHz, DMSO-$d_6$) δ 7.53 (1H, s), 7.35–7.42 (3H, m), 6.23 (1H, broad s), 5.32–5.33 (1H, m), 4.90 (1H, dd, J=3.2, 12.4 Hz), 4.60 (1H, dd, J=1.2, 12.4 Hz).

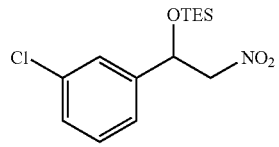

[1-(3–Chloro-phenyl)-2-nitro-ethoxy]-triethyl-silane: To a solution of 1-(3-chlorophenyl)-2-nitro-ethanol (26 g, 0.14 mol) in DMF (50 mL) were added imidazole (28.6 g, 0.42 mol) and chlorotriethylsilane (25.3 g, 0.17 mol). The reaction mixture was stirred at room temperature for 2 h. After quenching with water, the mixture was extracted with ethyl acetate. The combined organic layers were washed with water and brine, dried over $Na_2SO_4$, and filtered. After removal of solvent, the crude product was purified by flash chromatography (2% EtOAc/hexane) to yield the title compound (37 g, 91%) as a colorless oil. $^1$H NMR (300 MHz, CDCl$_3$) δ 7.40 (1H, s), 7.27–7.32 (3H, m), 5.40 (1H, dd, J=3.2, 9.5 Hz), 4.51 (1H, dd, J=9.5, 12.1 Hz), 4.36 (1H, dd, J=3.3, 12.1 Hz), 0.85 (9H, t, J=7.5 Hz), 0.54 (6H, q, J=7.5 Hz).

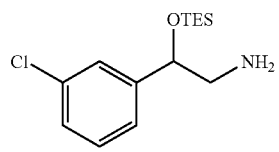

2-(3–Chloro-phenyl)-2-triethylsilanyloxy-ethylamine: Raney nickel (1 g) was washed with distilled water five times and methanol three times. [1-(3–Chlorophenyl)-2-nitro-ethoxy]-triethyl-silane (10 g, 0.032 mol) and Raney nickel in methanol (100 mL) was hydrogenated (35 psi) at room temperature for 14 h. The reaction mixture was filtered through a pad of celite and rinsed with methanol. Concentration of the filtrate to dryness gave the title compound (5.6 g, 62%) as a colorless oil which was used for the next step without purification. $^1$H NMR (300 MHz, CDCl$_3$) δ 7.32 (1H, s), 7.18–7.26 (3H, m), 4.70 (1H, t, J=5.8 Hz), 2.86 (2H, m), 0.89 (9H, t, J=7.9 Hz), 0.56 (6H, q, J=7.8 Hz). LRMS (M+H)$^+$ m/z 286.

General Procedure for the Preparation of 2-Hydroxy-2-(substituted-phenyl)-ethylamines:

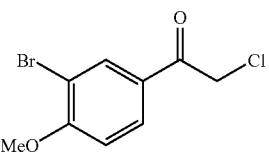

4-methoxy-3-bromophenyl chloroacetophenone: To a suspension of AlCl$_3$ (13.4 g, 0.10 mol) in methylene chloride (40 mL) was added a solution of 2-bromoanisole (12.5 mL, 0.10 mol) and chloroacetyl chloride (8 mL, 0.10 mol) at 0° C. The solution was warmed to ambient temperature for two hours and poured onto ice and extracted with methylene chloride, washed with saturated sodium bicarbonate solution, brine, and dried over MgSO₄. The solution was filtered, concentrated and crystalized from EtOH to give 15.37 g of white solid. LRMS [M−H]-260.8; IR (KBr) 1697, 1048, 1255 cm⁻¹; ¹H NMR (300 MHz, CDCl₃) δ 8.18 (s, 1H), 7.94 (dd, J=8.67 Hz, 1H), 6.96 (d, J=8.67 Hz, 1H), 4.62 (s, 2H), 3.98 (s, 3H); ¹³C NMR (CDCl₃, 75.5 Hz) δ 188.8, 160.3, 134.1, 129.9, 128.2, 112.4, 111.3, 56.6, 45.3.

General Procedure for Chiral Reduction of Chloroketones and Ammonolysis:

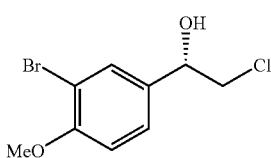

(S)-1-[4-methoxy-3-bromophenyl]-2-chloro ethanol: To a solution of (S)-Methyl-CBS-oxazaborolidine (1M in toluene, 0.745 mL, 0.745 mmol) and BH₃-THF (8 mL, 8 mmol) was added at the same time a solution of BH₃-THF (19 mL, 19 mmol) and a solution of the chloroketone (10.03 g, 37.98 mmol) in 19 mL of THF. Both solutions were added dropwise over 30 minutes. The solution was stirred for 1 hour and quenched with the slow addition of methanol (50 mL). The solution was concentrated and the residue chromatographed over a short silica gel column (1:1 hexane/ethyl acetate) to give a quantitative yield (10.0 g) of chlorohydrin as a clear oil. IR (KBr) 1053, 1258, 3406 cm⁻¹; ¹H NMR (300 MHz, CDCl₃) δ 7.59 (s, 1H), 7.30 (dd, J=2.16 Hz, 1H), 6.90 (d, J=8.46 Hz, 1H), 4.83 (dd, J=3.57 Hz, 1H), 3.90 (s, 3H), 3.64 (ddd, J=3.6, 11.1, 8.7, 2H), 2.04 (b s, 1H). ¹³C NMR (CDCl₃, 75.5 MHz) δ 155.9, 133.5, 131.1, 126.3, 111.9, 73.1, 60.4, 56.3, 50.7.

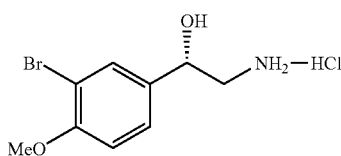

(S)2-Amino-1-[3-chloro-4-methoxyphenyl]ethanol Hydrochloride: To a solution of the chlorohydrin (10.0 g, 37.9 mmol) in 120 mL of methanol at −40° C. was added 100 grams of ammonia. The solution was sealed in a pressure bottle and warmed to ambient temperature and stirred for 48 hours. The solution was cooled and opened. The ammonia was allowed to evaporate and solution concentrated. The residue was crystalized from ethanol/ethyl acetate to give 3.83 g of white solid (35%). The material was reacted with Boc₂O in ethyl acetate and saturated sodium bicarbonate and analyzed by chiral HPLC using a chiralcel OJ column using 95% hexane/ethanol as elutant and determined to by 98% ee. Additional crops were collected—2.96 g and 1.41 g for a total of 75% yield. LRMS [M+H]+246; IR (cm⁻¹, KBr) 1055, 1261, 3001, 2948, 3356; ¹H NMR (500 MHz, DMSO) δ 8.09 (b s, 2H), 7.58 (s, 1H), 7.36 (dd, J=2.05, 6.45 Hz, 1H), 7.11 (d, J=8.5 Hz, 1H), 6.10 (s, 1H), 4.80 (m, 1H), 3.84 (s, 3H), 3.00 (ddd, J=2.7, 12.6, 9.5 Hz, 2H); C NMR (DMSO, 75.5 MHz) δ 154.8, 135.4, 130.4, 126.6, 112.4, 110.4, 67.9, 56.2, 45.4.

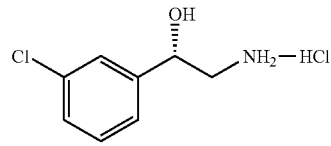

(S)2-Amino-1-[3-chlorophenyl]ethanol Hydrochloride: was prepared according to the general procedure outlined above. LRMS [M+H]+172; IR (KBr, cm−1) 3048, 3351, 2952; ¹H NMR (300 MHz, MeOD) δ 7.48 (s, 1H), 7.35 (m, 3H), 3.31 (ddd, J=1.5, 3.12, 9.15 Hz 2H).

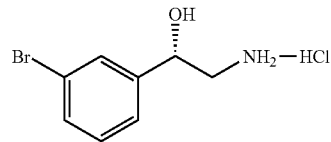

(S)-2-Amino-1-[3-bromophenyl]ethanol Hydrochloride: was prepared according to the general procedure outlined above. LRMS [MH]+217.9; IR (KBr, cm−1) 3025, 3443, 2891; ¹H NMR (500 MHz, DMSO) δ 7.93 (b s, 2H), 7.60 (s, 1H), 7.52 (d, 1H), 7.41 (s, 1H), 7.35 (d, J=7.7 Hz, 1H) 6.17 (s, 1H), 4.82 (m, 1H), 3.08 (ddd, J=2.6, 12.7, 9.6 Hz, 2H); ¹³C NMR (DMSO, 75.5 MHz) δ 144.4, 130.5, 128.7, 125.0, 121.6, 68.3, 45.1.

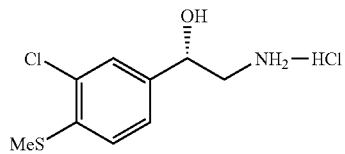

(S)-2-Amino-1-[3-chloro-4-methylthiophenyl]ethanol Hydrochloride: was prepared according to the general procedure outlined above. LRMS [M+H]+217.9; IR (KBr, cm−1) 3007, 3358; ¹H NMR (500 MHz, DMSO) δ 8.12 (b s, 2H), 7.46 (s, 1H), 7.37 (s, 1H), 7.35 (d, 1H) 6.19 (d, 1H), 4.83 (m, 1H), 3.01 (ddd, J=3.2, 12.8, 9.3 Hz, 2H); ¹³C NMR (DMSO, 75.5 MHz) δ 139.6, 136.5, 129.8, 126.6, 125.4, 68.0, 45.2, 14.2.

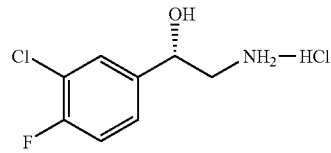

(S)-2-Amino-1-[3-chloro-4-fluoro-phenyl]ethanol Hydrochloride: was prepared according to the general procedure outlined above. LRMS [M+H]+189.9; IR (KBr, cm−1) 1509, 3008, 3359; ¹H NMR (500 MHz, DMSO) δ 8.21 (b s, 2H), 7.61 (d, J=7.85 Hz, 1H), 7.42 (m, 2H), 6.29 (s, 1H), 4.88 (m, 1H), 3.03 (ddd, J=3.4, 12.8, 9.2 Hz, 2H);

¹³C NMR (DMSO, 75.5 MHz) δ 157.5, 155.5, 139.7, 128.1, 126.7, 119.3, 116.7, 109.0, 67.8, 45.2.

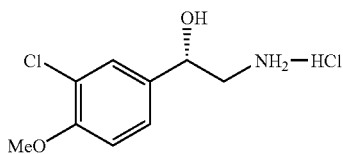

(S)-2-Amino-1-[3-chloro-4-methoxyphenyl]ethanol Hydrochloride: was prepared according to the general procedure outlined above. LRMS [M+H]+202; IR (KBr, cm−1) 3354, 3003, 2949, 1288, 1064; ¹H NMR (500 MHz, DMSO) δ8.18 (brs, 3H), 7.43 (d, J=2.0 Hz, 1H), 7.31 (dd, J=8.5, 2.0 Hz, 1H), 7.14 (d, J=5.1 Hz, 1H), 6.11 (s, 1H), 4.81 (m, 1H), 3.84 (s, 3H), 2.99 (dd, J=13, 3.5 Hz, 1H), 2.83 (dd, J=12.5, 9 Hz, 1H); ¹³C NMR (DMSO, 125 MHz) δ 153.9, 135.0, 127.3, 125.8, 120.8, 112.6, 68.0, 56.1, 45.5; Elemental Analysis Calcd for $C_9H_{12}ClNO_2$—HCl: C, 45.39; H, 5.50; N, 5.88. Found: C, 45.38; H, 5.43; N, 5.70.

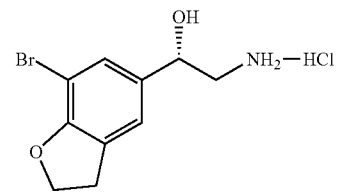

(S)-2-Amino-1-(7-bromo-2,3-dihydrobenzfuran-5-yl)-2-aminoethanol Hydrochloride: was prepared according to the general procedure outlined above. LRMS [M+H]+258; IR (KBr, cm−1) 3349, 3006, 2928, 1485, 1045, 983; ¹H NMR (500 MHz, DMSO) δ 8.13 (brs, 3H), 7.29 (s, 1H), 7.23 (s, 1H), 6.08 (d, J=4 Hz, 1H), 4.76 (m, 1H), 4.61 (t, J=9 Hz, 2H), 3.29 (t, J=9 Hz, 2H), 2.96 (dd, J=13, 3.5 Hz, 1H), 2.82 (dd, J=13, 9.5 Hz, 1H); C NMR (DMSO, 125 MHz) δ 156.3, 135.9, 129.1, 128.1, 122.1, 100.9, 71.5, 68.2, 45.6, 29.9; Elemental Analysis Calcd for $C_{10}H_{12}BrNO_2$—HCl: C, 40.77; H, 4.44; N, 4.75. Found: C, 40.77; H, 4.63; N, 4.63.

General Procedure for the Preparation of 2-Amino-3-(substituted-phenyl)-propanol:

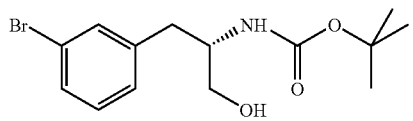

(S)-[2-(3-Bromo-phenyl)-1-hydroxymethyl-ethyl]-carbamic acid tert-butyl ester:

To a solution of (S)-3-(3-bromo-phenyl)-2-tert-butoxycarbonylamino-propinic acid (500 mg, 1.45 mmol) in THF (30 mL) was added borane-tetrahydrofuran complex (1.0 M solution) (4.35 mL, 4.35 mmol). The reaction mixture was stirred at room temperature for 14 h and quenched with acetic acid (1 mL). After removal of most solvent, the residue was extracted with EtOAc, washed with brine, dried over Na₂SO₄. After concentration, the crude product (400 mg, 83%) was used for the next step without purification. LCMS (M+H)⁺ m/z 330 (t=1.61 min

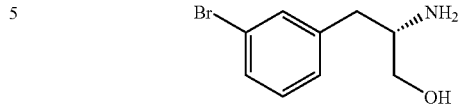

(S)-2-Amino-3-(3-bromo-phenyl)-propan-1-ol: To a solution of (S)-[2-(3-bromophenyl)-1-hydroxymethyl-ethyl]-carbamic acid tert-butyl ester (400 mg, 1.21 mmol) in methanol (30 mL) was added 4 M HCl in dioxane (2 mL, excess). The reaction mixture was stirred at room temperature for 14 h. After concentration in vacuo, the residue was used for the next step without purification. LCMS (M+H)⁺ m/z 230 (t=0.78 min.)

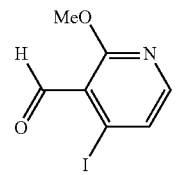

4-Iodo-2-methoxy-pyridine-3-carbaldehyde (WO 95/29917): A 5-liter three-necked round bottom flask was equipped with an overhead mechanical stirrer under nitrogen, the flask was charged with THF (1 L) and cooled to −78° C. To this stirred solution was added tert-butyllithium (1.7 M solution in pentane) (800 mL, 1.36 mol) via canula followed by 2-methoxypyridine (132.2 g, 1.21 mol) at −78° C. The mixture was stirred for 1 h at −78° C. To the mixture was added N-formyl-N,N',N'-trimethylethylenediamine (176 mL, 1.37 mol) dropwise at −78° C. The reaction mixture was stirred for ca. 30 min at −78° C. before warming to −23° C. over ca. 30 min. To the mixture at −23° C. was added ethylene glycol dimethyl ether (1 L) followed by n-butyllithium (2.5 M solution in hexane) (800 mL, 2.0 mol). The resulting mixture was stirred for ca. 2 h during which time the reaction mixture turned deep green. A 12-L 4-necked round flask was charged with iodine (571 g, 2.25 mol) and ethylene glycol dimethyl ether (2 L) and the resultant solution was cooled to −78° C. The contents of the 5-L flask were transferred via canula to the mixture of iodine and ethylene glycol dimethyl ether in the 12-L flask at −78° C. After the addition was complete, the reaction mixture was stirred for an additional 1 h at −78° C. The cooling bath was removed and the mixture was allowed to warm to about 0° C. and treated with 2 L of water and 2 L of 1 N hydrochloric acid. Methyl t-butyl ether (2 L) was added and the layers were separated. The aqueous layer was extracted with 2×1 L of methyl t-butyl ether. The combined organic layers were washed with saturated Na₂S₂O₃ (1.2 L), brine (1.2 L), dried over Na₂SO₄. After concentration in vacuo, the thick slurry was diluted with hexane (1 L). The mixture was cooled with an ice/water bath for ca. 30 min. The precipitate was filtered and dried in vacuum to yield the title compound as a light yellow solid. ¹H NMR (300 MHz, CDCl₃) δ 10.22 (s, 1H), 7.86 (1H, d, J=5.3 Hz), 7.54 (1H, d, J=5.3 Hz), 4.06 (3H, s). LCMS (M+H)+ m/z 364 (t=2.26 min.).

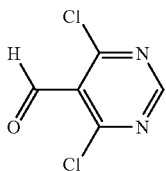

4,6-Dichloro-pyrimidine-5-carbaldehyde: DMF (7 mL, 0.09 mol) was added to POCl₃ (21 mL, 0.23 mol) at 0° C. The reaction mixture was stirred at room temperature for 0.5 h. 4,6-Dihydroxy-pyrimidine-5-carbaldehyde (5 g, 0.045 mol) was added in small portions. The reaction mixture was heated to 90° C. for 6 h and cooled to room temperature. A large excess of crushed ice was added to the reaction mixture very slowly under ice-bath. The mixture was extracted with CH₂Cl₂. The combined organic layers were washed with water, brine, and dried over Na₂SO₄. After concentration, the residue was purified by column chromatography (20% EtOAc/hexane) to yield the title compound (4 g, 50%). ¹H NMR (400 MHz, CDCl₃) δ 8.91 (1H, s), 7.87 (1H, s). LRMS (M+H)+ m/z 177.

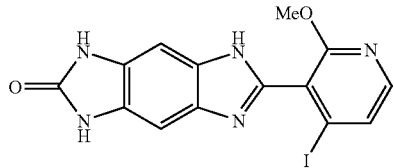

6-(4-Iodo-2-methoxy-pyridin-3-yl)-3,5-dihydro-1H-benzo[1,2-d;4,5-d]diimidazol-2-one: A 250 mg (1.0 mml) of the dianiline, and 281 mg (1.0 mml) of the iodoaldehyde were taken in 5 mL of methanol, and the reaction mixture was stirred at room temperature for 12 hr, solvent was evaporated to dryness, and the residue was chromatographed to furnish the product. LRMS [M+H]+408; ¹H NMR (400 MHz, CD₃OD) □ 8.13 (d, J=5.4 Hz, 2H), 7.73 (d, J=5.4 Hz, 2H), 7.42 (s, 2H), 3.96 (s, 3H).

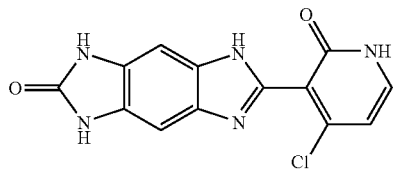

6-(4–Chloro-2-oxo-1,2-dihydro-pyridin-3-yl)-3,5-dihydro-1H-benzo [1,2-d;4,5-d]diimidazol-2-one: A 100 mg (0.245 mml) of the methoxy compound was treated with 3 mL of 4 N HCl in dioxane, to which was added 0.5 mL of water, and the mixture was heated at 80° C. for 4 hrs, solvent was evaported to dryness and the residue was used in the next reaction. LRMS [M+H]+302.

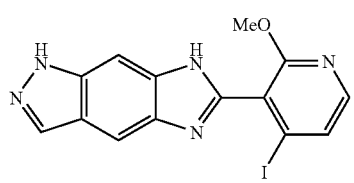

6-(2-Iodo-6-methoxy-phenyl)-1,7-dihydro-1,2,5,7-tetraaza-s-indacene:
To a solution of 1H-indazole-5,6-diamine (250 mg, 1.69 mmol) in methanol (80 mL) was added 2-hydroxy-4-iodo-pyridine-3-carbaldehyde (445 mg, 1.69 mmol). The reaction mixture was stirred at room temperature overnight. Concentration in vacuo, the residue was purified by prep. HPLC to yield the titled compound (416 mg, 63%). LCMS (t=0.81 min), [M+H]+392.

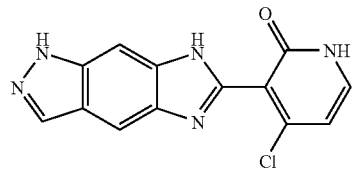

4–Chloro-3-(1,7-dihydro-1,2,5,7-tetraaza-s-indacene-6-yl)-1H-pyridin-2-one: A suspension of 6-(2-iodo-6-methoxy-phenyl)-1,7-dihydro-1,2,5,7-tetraaza-s-indacene (mg, mmol) in 4N HCl dioxane (15 mL) was heated to 80° C. for 4 h. Concentration in vacuo, the residue was used for the next step without purification. LCMS (t=0.76 min), [M+H]+ 286.

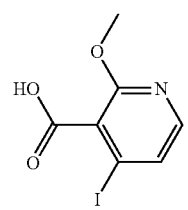

4-Iodo-2-methoxy-nicotinic acid: To a solution of 4-iodo-2-methoxy-pyridine-3-carbaldehyde (4.96 g, 18.9 mmol) in 22 mL tert.-butanol was added in this order 2-methyl-2-butene (30 mL of a 2 M solution in THF, 60 mmol), natriumdihydrogen-phosphate (5.7 g, 47.5 mmol), water (15 mL) and sodiumchlorite (3.9 g, 43 mmol). The mixture was stirred at ambient temperature for 1 hour, then poured on dilute aqueous formic acid. The mixture was extracted with ethyl acetate, the organic layer washed with water and brine and concentrated. The residue was dissolved in diisopropylether+dichloromethane (1+1) and extracted 3 times with half-concentrated aqueous NaOH solution. The combined aqueous layers were acidified with conc. HCl and extracted with ethyl acetate. The organic layers were washed with water and brine, then dried over sodium sulfate and concentrated to give 3.462 g of the title compound as a white solid (67%). ¹H NMR (500 MHz, CD₃OD) δ 7.83 (d, J=5.4 Hz, 1H), 7.43 (d, J=5.4 Hz, 1H), 3.94 (s, 3H);

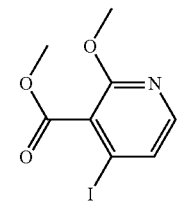

4-Iodo-2-methoxy-nicotinic acid methyl ester: To a solution of 4-iodo-2-methoxy-nicotinic acid (1.7 g, 6.1 mmol) in 50 mL of methanol (50 ml) was added trimethylsilyldiazomethane (15 mL of a 2M solution in hexanes, 30 mmol). The mixture was stirred at ambient temperature overnight, then concentrated. The crude product was purified by flash column chromatography on silica (eluent: hexanes-ethyl acetate-triethylamine 100-10-1, then 70-30-1). 1.685 g colorless solid were isolated (94%). $^1$H NMR (500 MHz, acetone-$d_6$) δ 7.93 (d, J=5.4 Hz, 1H), 7.50 (d, J=5.4 Hz, 1H), 3.92 (s, 3H), 3.90 (s, 3H);

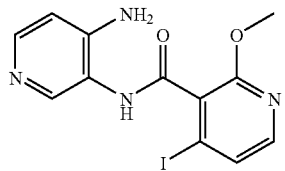

N-(4-Amino-pyridin-3-yl)-4-iodo-2-methoxy-nicotinamide (Scheme II): To a suspension of 3,4-diaminopyridine (1.8 g, 16.5 mmol) in 50 mL THF under an atmosphere of argon was added lithiumhexamethyldisilazane (40 mL of a 1M solution in hexanes, 40 mmol) and the mixture was stirred for 30 minutes at room temperature. A solution of 4-iodo-2-methoxy-nicotinic acid methyl ester (1.8 g, 6.35 mmol) in THF was added and the mixture stirred at room temperature for 4 hours. The mixture was poured on a saturated aqueous solution of ammonium chloride and extracted with ethyl acetate. The combined organic layers were washed with water and brine, then dried over sodium sulfate and concentrated. Flash column chromatography on silica (eluent: chloroform-methanol 100-0, then 95-5, 90-10, 80-20) gave 807.8 mg product as an off-white solid. LCMS [M+H]+371, T=0.72 min [YMC ODS-A C18 S7 3.0×50 mm column; 0–100% gradient over 2 min*; 5 mL/min flow rate].* Gradient begins with 10% methanol/90% water (0.1% TFA) and end with 90% methanol/10% water (0.1% TFA); $^1$H NMR (500 MHz, DMSO-$d_6$) δ 9.89 (s, 1H), 8.27 (s, 1H), 7.94 (m, 2H), 7.55 (d, J=5.45 Hz, 1H), 6.69 (d, J=5.5 Hz, 1H), 5.76 (s, 2H), 3.91 (s, 3H); A NOE enhancement was observed between the amide-NH and C(2)H of the pyridine, and between the NH2 group and C(5)H of the pyridine.

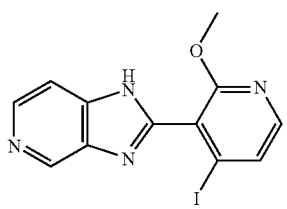

2-(4-Iodo-2-methoxy-pyridin-3-yl)-1H-imidazo[4,5-c] pyridine (Scheme II): To a solution of N-(4-amino-pyridin-3-yl)-4-iodo-2-methoxy-nicotinamide (612.6 mg, 1.655 mmol) in 10 mL pyridine at 0 C was added (slowly) 1 mL POCl$_3$. The mixture was stirred for 2 hours, during which time the cooling bath warmed to 10 C. The mixture was concentrated in vacuum to give 2.0 g of crude product as a black oil that was used as is. LCMS [M+H]+353, T=0.92 min [YMC ODS-A C18 S7 3.0×50 mm column; 0–100% gradient over 2 min*; 5 mL/min flow rate].* Gradient begin with 10% methanol/90% water (0.1% TFA) and end with 90% methanol/10% water (0.1% TFA);

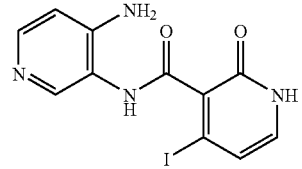

4-Iodo-2-oxo-1,2-dihydro-pyridine-3-carboxylic acid (3-amino-pyridin-4-yl)-amide (Scheme III): A solution of 2-(4-iodo-2-methoxy-pyridin-3-yl)-1H-imidazo[4,5-c]pyridine (2.0 g crude) in 1 M aqueous HCl was refluxed for 17 hours. The mixture was poured onto a mixture of saturated aqueous sodium bicarbonate solution and ethyl acetate. The insoluble product was filtered off, rinsed with water and dried. 346.7 mg of brown powder were isolated (54% over 2 steps). MS [M+H]+357, {M–H]–355; $^1$H NMR (500 MHz, DMSO-$d_6$) δ 12.24 (broad s, 1H), 9.82 (s, 1H), 8.03 (s, 1H), 7.94 (d, J=5.5 Hz, 1H), 7.23 (d, J=6.9 Hz, 1H), 6.72 (d, J=6.9 Hz, 1H), 6.64 (d, J=5.5 Hz, 1H), 6.06 (s, 2H); A NOE enhancement was observed between the amide-NH and C(2)H of the pyridine, and between the NH2 group and C(5)H of the pyridine.

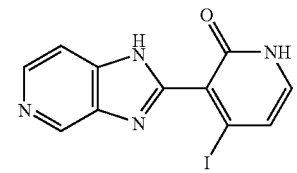

3-(1H-Imidazo[4,5-c]pyridin-2-yl)-4-iodo-1H-pyridin-2-one (Scheme III): To a solution of 4-iodo-2-oxo-1,2-dihydro-pyridine-3-carboxylic acid (4-amino-pyridin-3-yl)-amide (281 mg, 0.79 mmol) in 9 mL pyridine at 0 C was added (slowly) 0.5 mL POCl$_3$ (5.3 mmol). The mixture was stirred at 0 C for 2 hours, then poured on a mixture of ice and saturated aqueous sodium bicarbonate solution. The product precipitates as a colloid. All attempts to filter or extract the product failed. The mixture was concentrated in vacuum, water removed by aceotropic distillation with n-propanol and the crude mixture used as it is. LCMS [M+H]+339, T=0.54 min product and [M+H]+357, T=0.29 min unreacted starting material [YMC ODS-A C18 S7 3.0×50 mm column; 0–100% gradient over 2 min*; 5 mL/min flow rate].* Gradient begins with 10% methanol/90% water (0.1% TFA) and end with 90% methanol/10% water (0.1% TFA)

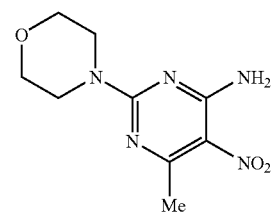

4-Amino-6-methyl-2-morpholin-4-yl-5-nitropyrimidine: To pressure vessel, a mixture of commercially available 4-amino-2-chloro-6-methyl-5-nitropyrimidine (2.00 g, 10.6 mmol) and morpholine (1.85 mL, 21.2 mmol) in absolute ethanol (40 mL) was stirred at 82° C. for 16 hours. Absolute ethanol was evaporated in vacuo and the crude product was dissolved in a mixture of THF:EtOAc and this then subjected on top of a silica gel pad. Elution with EtOAc gave, after evaporation, the title compound as a yellow solid (2.47 g, 97%): IR (KBr, cm$^{-1}$) 3468, 3307, 1615, 1560, 1247; $^1$H NMR (400 MHz, DMSO) δ 7.96 (s, 2H), 3.77 (br s, 4H), 3.62–3.60 (m, 4H), 2.53 (s, 3H); LCMS ($^+$ESI, M+H$^+$) m/z 240; HPLC: 100% (220 m).

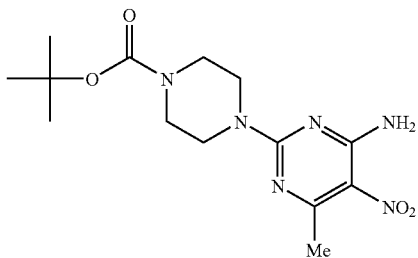

4-(5-Amino-4-methyl-6-nitro-pyrimidin-2-yl)-piperazine-1-carboxylic acid tert-butyl ester: To pressure vessel, a mixture of commercially available 4-amino-2-chloro-6-methyl-5-nitropyrimidine (2.00 g, 10.6 mmol) and Boc-piperazine (3.95 g, 21.2 mmol) in absolute ethanol (40 mL) was stirred at 83° C. for 16 hours. Absolute ethanol was evaporated in vacuo and the crude product was dissolved in a mixture of THF:EtOAc and this then subjected on top of a silica gel pad. Elution with EtOAc gave, after evaporation, the title compound as a yellow solid (3.46 g, 96%): IR (KBr, cm$^{-1}$) 3464, 3327, 2860, 1693, 1571, 1247; $^1$H NMR (400 MHz, DMSO) δ 7.98 (s, 2H), 3.79 (br s, 4H), 3.38 (br s, 4H), 2.55 (s, 3H), 1.43 (s, 9H); LCMS ($^+$ESI, M+H$^+$) m/z 283; HPLC: 98% (220 nm).

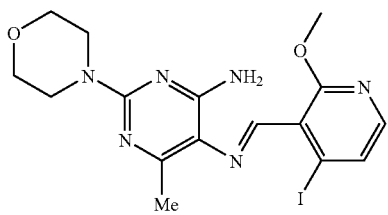

N$^5$-(4-Iodo-2-methoxy-pyridin-3-ylmethylene)-6-methyl-2-morpholin-4-yl-pyrimidine-4,5-diamine: To 4-amino-6-methyl-2-morpholin-4-yl-5nitropyrimidine (500 mg, 2.09 mmol) and 10% palladium on carbon (100 mg) were added methanol (10 mL) under nitrogen. The reaction mixture was stirred under hydrogen atmosphere (hydrogen balloon) for 22 hours. The solution was filtered through a pad of celite and the filtercake was washed with a small amount of MeOH. The product in MeOH was used for the next step without purification; LCMS ($^+$ESI, M+H$^+$) m/z 210; HPLC: 97% (220 nm). To the crude diamino in MeOH (50 mL) was added a solution of 4-iodo-2-methoxy-pyridine-3-carbaldehyde (604 mg, 2.30 mmol) in MeOH (10 mL) at 0° C. and stirred for 0.5 hour. The resulting mixture was allowed to warm to ambient temperature and stirred for 6 days in an open system exposed to air. The reaction mixture was cooled to 0° C. to afford a crystalline yellow solid, which was collected by filtration to give the title compound (830 mg, 87%): $^1$H NMR (400 MHz, DMSO) δ 8.43 (s, 1H), 7.85 and 7.62 (d, J=5.3, 1H), 6.23 (br s, 2H), 3.91 (s, 3H), 3.61 (s, 8H), 2.26 (s, 3H); LCMS ($^+$ESI, M+H$^+$) m/z 455.

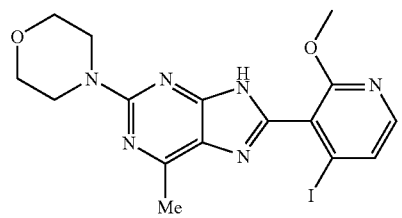

8-(4-Iodo-2-methoxy-pyridin-3-yl)-6-methyl-2-morpholin-4-yl-9H-purine: To a solution of N$^5$-(4-Iodo-2-methoxy-pyridin-3ylmethylene)-6-methyl-2-morpholin-4-yl-pyrimidine-4,5-diamine (140 mg, 0.31 mmol) in a mixture of MeOH:THF (20 mL: 10 mL) was added iodobenzene diacetate (198 mg, 0.62 mmol). After stirring at ambient temperature for 4 hours, the solvents were evaporated in vacuo and the crude was purified by preparative HPLC (see method below) to give the title compound as an amber solid (50 mg, 36%): IR (KBr, cm–1) 3420, 2853, 1618; $^1$H NMR (400 MHz, CDCl$_3$) δ 9.63 (s, 1H), 7.83 and 7.54 (d, J=5.3, 1H), 3.91 (s, 3H), 3.81–3.77 (m, 8H), 2.72 (s, 3H); LCMS ($^+$ESI, M+H$^+$) m/z 453; HPLC: 97% (220 nm).

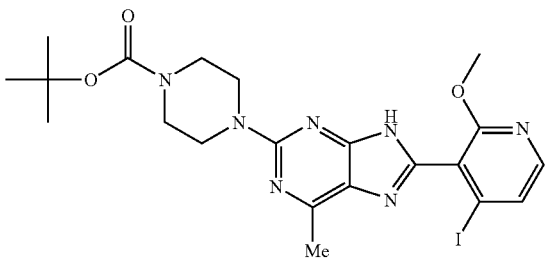

4-[8-(4-Iodo-2-methoxy-pyridin-3-yl)-6-methyl-9H-purin-2-yl]-piperazine-1-carboxylic acid tert-butyl ester: To a stirred solution of 4-(5-amino-4-methyl-6-nitro-pyrimidin-2-yl)-piperazine-1-carboxylic acid tert-butyl ester (3.18 g, 9.4 mmol) in methanol (200 mL) and 10% palladium on carbon (180 mg) were added methanol (10 mL) under nitrogen. The reaction mixture was stirred under hydrogen atmosphere (hydrogen balloon) for 18 hours. The solution was filtered through a pad of celite and the filtercake was washed with a small amount of MeOH. This solution was cooled to 0° C. and the 4-iodo-2-methoxy-pyridine-3-carbaldehyde (2.47 g, 9.4 mmol) in methanol (50 mL) was added to the reaction mixture and stirred at 23° C. for 18 hours. Then iodobenzene diacetate (3.03 g, 9.4 mmol) was added and the reaction mixture was stirred at 23° C. for 5 hours. MeOH was evaporated in vacuo and the crude material was purified on silica gel column using EtOAc:Hex (1:2 to 1:1 gradient) to give the title compound as a yellow solid. (2.75 g, 53%). HPLC 98%. LCMS ($^+$ESI, M+H$^+$) m/z 552; IR (KBr, cm$^{-1}$) 3177, 2976, 1699, 1558, 1223; $^1$H NMR (400 MHz, DMSO) δ 12.92 (s, 1H), 8.0 (d, J=5.1 Hz, 1H), 7.64 (d, J=5.6 Hz, 1H), 3.81 (s, 3H), 3.73 (br s, 4H), 3.43 (br s, 4H), 2.57 (s, 3H), 1.44 (s, 9H).

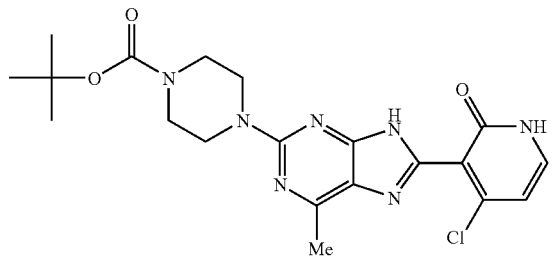

4-[8-(4-Chloro-2-oxo-1,2-dihydro-pyridin-3-yl)-6-methyl-9H-purin-2-yl]-piperazine-1-carboxylic acid t-butyl ester: To a solution of 4-[8-(4-iodo-2-methoxy-pyridin-3-yl)-6-methyl-9H-purin-2-yl]-piperazine-1-carboxylic acid tert-butyl ester (1.4 g, 2.54 mmol) in glacial acetic acid (30 mL) was added 11.6 M HCl (30 mL). The reaction mixture was stirred at 75° C. for 6 hours in a sealed tube and concentrated. The residue was dissolved in CH$_2$Cl$_2$ (250 mL) followed by the addition of triethylamine (2.78 mL, 20 mmol). The solution was cooled to 0° C. and di t-butyl dicarbonate (573 mg, 2.63 mmol) was added. The reaction mixture was stirred at 23° C. for 2 hours, poured on saturated NaHCO$_3$ solution and extracted with CH$_2$Cl$_2$ (3×200 mL). The combined organic layers, were dried over MgSO$_4$ and concentrated in vacuo to give the title compound as a yellow solid. (0.691 g, 62%). HPLC 93%; LCMS ($^+$ESI, M+H$^+$) m/z 446; IR (KBr, cm$^{-1}$) 3431, 2974, 1700, 1506, 1229; $^1$H NMR (400 MHz, DMSO+D$_2$O) δ 7.64 (d, J=7.0 Hz, 0.7H), 7.32 (d, J=7.0 Hz, 0.3H), 6.89 (d, J=7.0 Hz, 0.3H), 6.59 (d, J=7.0 Hz, 0.7H), 3.75 (br s, 4H), 3.45 (br s, 4H), 2.60 (s, 3H), 1.45 (s, 9H).

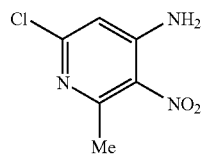

6-Chloro-2-methyl-3-nitro-pyridin-4-ylamine (Scheme IX): To a pressure vessel, a degassed solution of 2,6-dichloro-3-nitro-pyridin-4-ylamine (3.0 g, 14.4 mmol) (R. J. Rousseau and R. K. Robins *J. Heterocyclic Chem.* 2, 1965, 196) and tetrakis(triphenylphosphine)palladium(0) (1.67 g, 1.44 mmol) in DMF (45 mL) was stirred at room temperature. To this mixture was added dropwise a solution of trimethylaluminium (7.93 mL, 15.8 mmol, 2M in toluene). The resulting mixture was sealed and heated at 70° C. for 3 hours. The reaction mixture was poured into ice/water (800 mL). The organic material was extracted with EtOAc (5×200 mL). The combined organic layers were dried (MgSO$_4$) and concentrated in vacuo. The crude material was purified on silica gel dry column using EtOAc:Hexane gradient (1:9) to (3:7) to afford the desired compound as a yellow solid (1.20 g, 45%), HPLC: 99% (220 nm), LCMS ($^+$ESI, M+H$^+$) m/z 188, IR (KBr, cm$^{-1}$) 3431, 3310, 3172, 1653, 1506, 1264; $^1$H NMR (400 MHz, CDCl$_3$) δ 7.19 (s, 1H), 6.57 (br s, 2H), 2.63 (s, 3H).

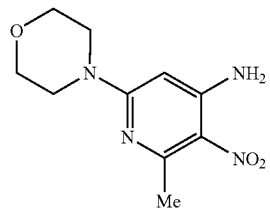

2-Methyl-6-morpholin-4-yl-3-nitro-pyridin-4-ylamine (Scheme IX): To a pressure vessel, a mixture of 6-chloro-2-methyl-3-nitro-pyridin-4-ylamine (0.75 g, 4.00 mmol) and morpholine (1.40 mL, 16.0 mmol) in absolute ethanol (16 mL) was stirred at 120° C. for 3 days. Absolute ethanol was evaporated in vacuo and the crude product was dissolved in a mixture of THF:EtOAc and this then subjected on top of a silica gel pad. Elution with EtOAc gave, after evaporation, the title compound as a yellow solid (0.89 g, 93%): IR (KBr, cm$^{-1}$) 3460, 3330, 1627, 1597, 1553, 1233, 1113; $^1$H NMR (400 MHz, DMSO) δ 7.13 (s, 2H), 5.89 (s, 1H), 3.66–3.63 (m, 4H), 3.46–3.44 (m, 4H), 2.50 (s, 3H); LCMS ($^+$ESI, M+H$^+$) m/z 239; HPLC: 99% (220 nm).

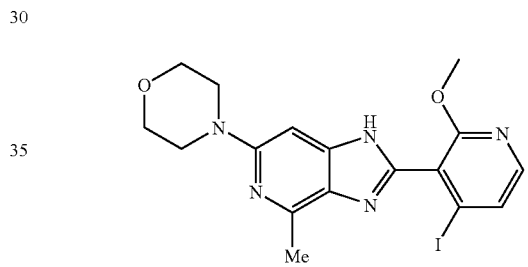

2-(4-Iodo-2-methoxy-pyridin-3-yl)-4-methyl-6-morpholin-4-yl-1H-imidazo[4,5-c]pyridine (Scheme IX): To 2-methyl-6-morpholin-4-yl-3-nitro-pyridin-4-ylamine (220 mg, 0.924 mmol) and 10% palladium on carbon (50 mg) were added methanol (10 mL) under nitrogen. The reaction mixture was stirred under hydrogen atmosphere (hydrogen balloon) for 18 hours. The solution was filtered through a pad of celite and the filtercake was washed with a small amount of MeOH. The product in MeOH was concentrated and used for the next step without purification; LCMS ($^+$ESI, M+H$^+$) m/z 209. To the crude diamino in MeOH (5 mL) was added a solution of 4-iodo-2-methoxy-pyridine-3-carbaldehyde (267 mg, 1.02 mmol) in MeOH (5 mL) at 0° C. and stirred for 0.5 hour. The resulting mixture was allowed to warm to ambient temperature and stirred for 4 days in an open system exposed to air. The reaction mixture was then heated to 50° C. and stirred for 2 days. MeOH was evaporated in vacuo and the crude was purified on silica gel column using CH$_2$Cl$_2$:MeOH (95:5 gradient) to give the title compound as a yellow solid (332 mg, 80%): IR (KBr, cm$^{-1}$) 1624, 1554, 1458, 1378; $^1$H NMR (400 MHz, DMSO) δ 12.46 (s, 1H), 8.00 and 7.64 (d, J=5.5, 1H), 6.54 (s, 1H), 3.80 (s, 3H), 3.74–3.72 (m, 4H), 3.38–3.36 (m, 4H), 2.58 (s, 3H); LCMS ($^+$ESI, M+H$^+$) m/z 452; HPLC: 97% (220 nm).

EXAMPLE 1

Scheme III

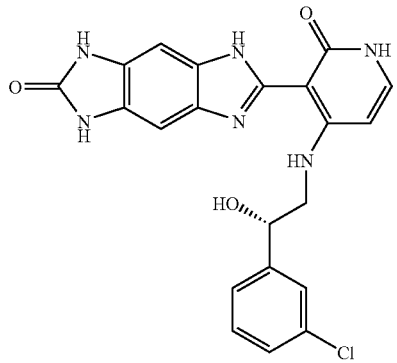

6-{4-[(S)-2-(3–Chloro-phenyl)-2-hydroxy-ethylamino]-2-oxo-1,2-dihydro-pyridin-3-yl}-3,5-dihydro-1H-benzo[1,2-d;4,5-d]diimidazol-2-one: To a stirred solution of 74 mg (0.245 mmol) of the chloropyridone in 2 mL of N-methylpyrrolidine was added 3 drops of N-methylmorpholine followed by 108 mg (0.612 mmol) of the (S)-2-(3–Chlorophenyl)-2-hydroxy-ethylamine, and the mixture was heated at 80° C. for 14 hrs, cooled, and residue was subjected to preparative HPLC to furnish the product. LRMS [M+H]+ 437; $^1$H NMR (400 MHz, CD$_3$OD) δ 7.27–7.47 (m, 6H), 6.24 (d, J=7.68 Hz, 1H), 4.91 (m, 1H), 3.56 (m, 2H).

EXAMPLE 2

Scheme III

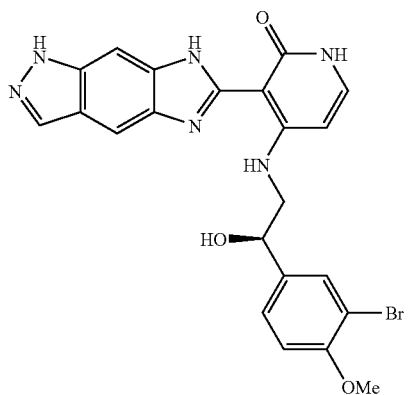

4-[(S)-2-(3-Bromo-4-methoxy-phenyl)-2-hydroxy-ethylamino]-3-(1,7-dihydro-1,2,5,7-tetraaza-s-indacen-6-yl)-1H-pyridin-2-one: The mixture of crude 4-chloro-3-(1,7-dihydro-1,2,5,7-tetraaza-s-indacen-6-yl)-1H-pyridin-2-one hydrochloric acid salt (80 mg, 0.25 mmol), (S)-2-amino-1-(3-bromo-4-methoxy-phenyl)-ethanol hydrochloric acid salt (105 mg, 0.37 mmol), N-methyl morpholine (0.5 ml, excess), and acetonitrile (15 mL) was heated to 80° C. overnight and cooled to room temperature. After concentration in vacuo, the residue was purified by prep. HPLC to yield the titled compound (79 mg, 66%). $^1$H NMR (400 MHz, CD$_3$OD) δ 8.13 (s, 1H), 7.85 (s, 1H), 7.69 (narrow d, J=2.0 Hz, 1H), 7.59 (s, 1H), 7.40 (dd, J=2.0, 8.5 Hz, 1H), 7.29 (d, J=7.6 Hz, 1H), 6.96 (d, J=8.5 Hz, 1H), 6.22 (d, J=7.6 Hz, 1H), 4.93 (m, 1H), 3.80 (s, 3H), 3.66 (d, J=6.0 Hz, 2H). LCMS (t=1.39 min), [M+H]$^+$495.

EXAMPLE 3

Scheme III

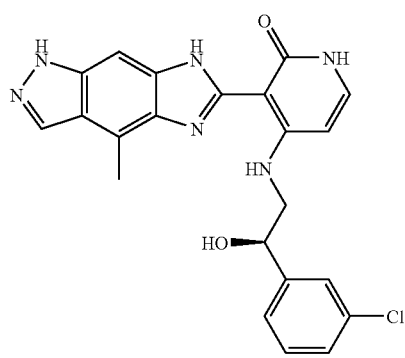

4-[(S)-2-(3–Chloro-phenyl)-2-hydroxy-ethylamino]-3-(1,7-dihydro-1,2,5,7-tetraaza-s-indacen-6-yl)-1H-pyridin-2-one: The mixture of crude 4-chloro-3-(1,7-dihydro-1,2,5,7-tetraaza-s-indacen-6-yl)-1H-pyridin-2-one hydrochloric acid salt (80 mg, 0.25 mmol), (S)-2-amino-1-(3-chlorophenyl)-ethanol hydrochloric acid salt (80 mg, 0.38 mmol), N-methyl morpholine (0.5 ml, excess), and acetonitrile (15 mL) was heated to 80° C. overnight and cooled to room temperature. After concentration in vacuo, the residue was purified by prep. HPLC to yield the titled compound (64 mg, 61%). $^1$H NMR (400 MHz, CD$_3$OD) δ 8.16 (s, 1H), 7.90 (s, 1H), 7.62 (s, 1H), 7.59 (s, 1H), 7.54 (s, 1H), 7.27–7.41 (m, 4H), 6.21 (d, J=7.6 Hz, 1H), 4.99 (m, 1H), 3.60–3.71 (m, 2H). LCMS (t=1.44 min), [M+H]$^+$421.

EXAMPLE 4

Scheme III

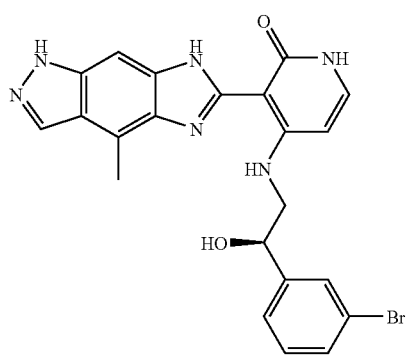

4-[(S)-2-(3-Bromo-phenyl)-2-hydroxy-ethylamino]-3-(1,7-dihydro-1,2,5,7-tetraaza-s-indacen-6-yl)-1H-pyridin-2-one: The mixture of crude 4-chloro-3-(1,7-dihydro-1,2,5,7-tetraaza-s-indacen-6-yl)-1H-pyridin-2-one hydrochloric acid salt (80 mg, 0.25 mmol), (S)-2-amino-1-(3-bromophenyl)-ethanol hydrochloric acid salt (96 mg, 0.37 mmol), N-methyl morpholine (0.5 ml, excess), and acetonitrile (15 mL) was heated to 80° C. overnight and cooled to room temperature. After concentration in vacuo, the residue was purified by prep. HPLC to yield the titled compound (73 mg, 63%). $^1$H NMR (400 MHz, CD$_3$OD) δ 8.08 (s, 1H), 7.46 (s, 1H), 7.44 (s, 1H), 7.21–7.40 (m, 5H), 6.14 (d, J=7.5 Hz, 1H), 4.97 (m, 1H), 3.60–3.68 (m, 2H). LCMS (t=1.46 min), [M+H]+465.

EXAMPLE 5

Scheme III

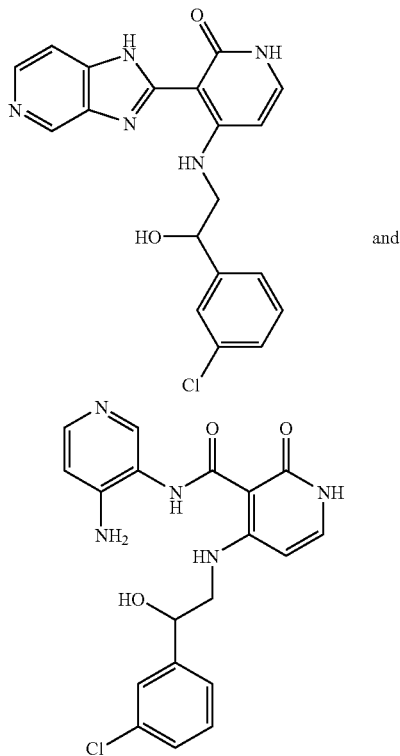

4-[2-(3–Chloro-phenyl)-2-hydroxy-ethylamino]-3-(1H-imidazo[4,5-c]pyridin-2-yl)-1H-pyridin-2-one trifluoroacetate salt: To a suspension of 0.2 mmol of the crude 3-(1H-imidazo[4,5-c]pyridin-2-yl)-4-iodo-1H-pyridin-2-one (<0.26 mmol) and 4-iodo-2-oxo-1,2-dihydro-pyridine-3-carboxylic acid (3-amino-pyridin-4-yl)-amide in 3 mL DMF was added 0.1 mL triethylamine (0.72 mmol) and 200 mg 2-(3-chlorophenyl)-2-triethylsilanyloxy-ethylamine (0.70 mmol). The mixture was stirred under argon at 80 C overnight. Volatile components were evaporated under a stream of nitrogen. The crude product was purified by preparative HPLC [XTERRA C-18 5 μm, 30×100 mm, 20% solvent B—100% solvent B gradient over 12 min; 40 mL/min flow rate, solvent A=10% methanol/90% water (0.1% TFA), solvent B=90% methanol/10% water (0.1% TFA)] to give 3.2 mg pale brown solid 4-[2-(3-chlorophenyl)-2-hydroxy-ethylamino]-3-(1H-imidazo[4,5-c]pyridin-2-yl)-1H-pyridin-2-one LCMS [M+H]+382, T=1.20 min and 9.6 mg brown film 4-[2-(3-chloro-phenyl)-2-hydroxy-ethylamino]-2-oxo-1,2-dihydro-pyridine-3-carboxylic acid (4-amino-pyridin-3-yl)-amide LCMS [M+H]+400, T=1.10 min. [YMC ODS-A C18 S7 3.0×50 mm column; 0–100% gradient over 2 min*; 5 mL/min flow rate].* Gradient begins with 10% methanol/90% water (0.1% TFA) and end with 90% methanol/10% water (0.1% TFA);

EXAMPLE 6

Scheme III

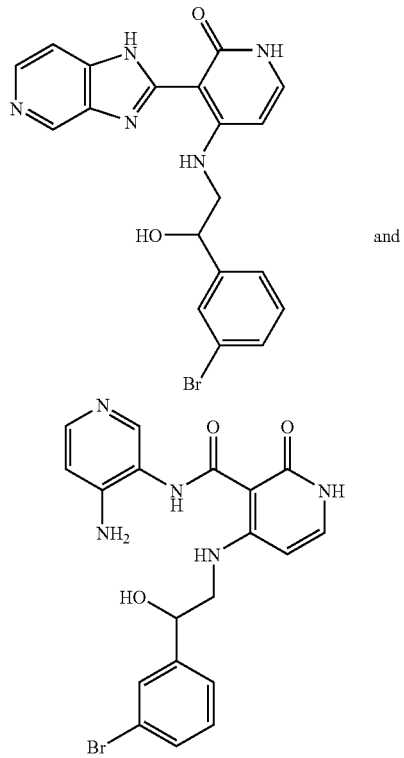

4-[2-(3-Bromo-phenyl)-2-hydroxy-ethylamino]-3-(1H-imidazo[4,5-c]pyridin-2-yl)-1H-pyridin-2-one trifluoroacetate: Following the procedure described above using 200 mg 2-amino-1-(3-bromo-phenyl)-ethanol (0.93 mmol) gave 15.0 mg 4-[2-(3-bromo-phenyl)-2-hydroxy-ethylamino]-3-(1H-imidazo[4,5-c]pyridin-2-yl)-1H-pyridin-2-one LCMS [M+H]+426, 428, T=1.22 min and 51.7 mg 4-[2-(3-bromophenyl)-2-hydroxy-ethylamino]-2-oxo-1,2-dihydro-pyridine-3-carboxylic acid (4-amino-pyridin-3-yl)-amide LCMS [M+H]+444, 446, T=1.14 min. [YMC ODS-A C18 S7 3.0×50 mm column; 0–100% gradient over 2 min*; 5 mL/min flow rate].* Gradient begins with 10% methanol/90% water (0.1% TFA) and end with 90% methanol/10% water (0.1% TFA); $^1$H NMR of imidazo[4,5-c]pyridin product (500 MHz, DMSO-d$_6$) 4:3 mixture of 2 tautomeres "a" and "b" δ 14.9 (broad s, 1H a+b), 13.97 (s, 1H, a), 13.86 (s, 1H, b), 11.46 (d, J=6.5 Hz, 1H, b), 11.42 (d, J=6.0 Hz, 1H, a), 10.68 (t, J=5.0 Hz, 1H, b), 10.59 (t, J=5.0 Hz, 1H, a), 9.16 (s, 1H, a), 9.07 (s, 1H, b), 8.52 (d, J=6.4 Hz, 1H, a+b), 8.15 (d, J=6.4 Hz, 1H, a), 7.93 (d, J=6.5 Hz, 1H, b), 7.72 (s, 1H, a+b), 7.53 (d, J=7.6 Hz, 1H, a+b), 7.46 (m, 2H, a+b), 7.33 (t, J=7.8 Hz, 1H, a+b), 6.26 (d, J=7.6 Hz, 1H, a+b), 6.00 (broad s, 1H, a+b), 4.95 (broad s, 1H, a+b), 3.75 (m, 1H, a+b), 3.59 (m, 1H, a+b); $^1$H NMR of "ring-open amide" product (500 MHz, DMSO-d$_6$) δ 13.43 (broad s, 1H), 12.65 (s, 1H), 11.30 (d, J=6.0 Hz, 1H), 10.52 (t, J=5.3 Hz, 1H), 8.51 (s, 1H), 8.09 (d, J=6.8 Hz, 1H), 7.7 (broad s, 2H), 7.64 (s, 1H), 7.46 (m, 2H), 7.38, (t, J=6.9 Hz, 1H), 7.31 (t, J=7.83 Hz, 1H), 6.97 (d, J=6.8 Hz, 1H), 6.14 (d, J=7.6 Hz, 1H), 5.89 (broad s, 1H), 4.80 (dd, J=7.8, 3.8 Hz, 1H), 3.55 (m, 1H), 3.37 (m, 1H).

EXAMPLE 7

Scheme III

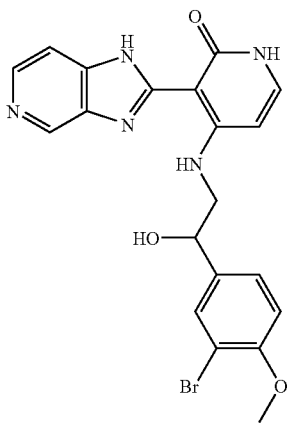

and

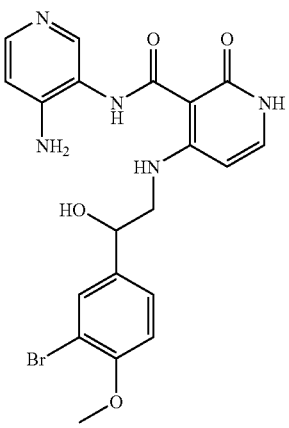

4-[2-(3-Bromo-4-methoxy-phenyl)-2-hydroxy-ethylamino]-3-(1H-imidazo[4,5-c]pyridin-2-yl)-1H-pyridin-2-one trifluoroacetate salt: Following the procedure described above using 200 mg 2-(3-bromo-4-methoxy-phenyl)-2-triethylsilanyloxy-ethylamine (0.55 mmol) gave 3.0 mg 4-[2-(3-bromo-4-methoxy-phenyl)-2-hydroxy-ethylamino]-3-(1H-imidazo[4,5-c]pyridin-2-yl)-1H-pyridin-2-one LCMS [M+H]+456, 458, T=1.16 min and 10.7 mg 4-[2-(3-bromo-4-methoxy-phenyl)-2-hydroxy-ethylamino]-2-oxo-1,2-dihydro-pyridine-3-carboxylic acid (4-amino-pyridin-3-yl)-amide LCMS [M+H]+474, 476, T=1.07 min. [YMC ODS-A C18 S7 3.0×50 mm column; 0–100% gradient over 2 min*; 5 mL/min flow rate].* Gradient begins with 10% methanol/90% water (0.1% TFA) and end with 90% methanol/10% water (0.1% TFA).

EXAMPLE 8

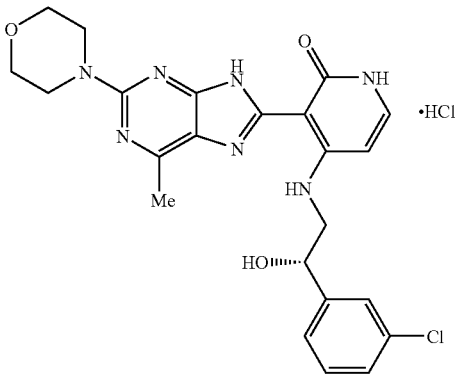

4-[2-(3–Chloro-phenyl)-2(S)-hydroxy-ethylamino]-3-(6-methyl-2-morpholin-4-yl-9H-purin-8-yl)-1H-pyridin-2-one hydrochloride: To a solution of 8-(4-iodo-2-methoxy-pyridin-3-yl)-6-methyl-2-morpholin-4-yl-9H-purine (115 mg, 0.254 mmol) in glacial acetic acid (5 mL) was added 5 mL of 11.6 M HCl in a pressure bottle. The vessel was sealed and heated to 85° C. for 15 hours. The reaction mixture was cooled and the vessel opened and concentrated in vacuo to give 117 mg of crude material which was used for the next step without purification. LCMS (+ESI, M+H+) m/z 347.

To a solution of the crude pyridone (0.254 mmol) in a mixture of CH$_3$CN:DMSO (5 mL:1 mL) was added triethylamine (0.35 mL, 2.54 mmol) and (S)-2-amino-1-(3-chloro-phenyl)-ethanol hydrochloride (69 mg, 0.331 mmol). The reaction tube was sealed and the mixture stirred at 80° C. for 20 hours. The cooled mixture was concentrated in vacuo and the crude was purified by preparative HPLC (see method below) to give pure product. This solid was dissolved in dioxane and a solution of 1N HCl in EtOH was added to form the hydrochloride salt, which was concentrated. i-PrOH was added to the solid, the solution was cooled to 0° C., filtrated and dried in vacuo to afford the above title salt as an amber solid (14 mg, 11%): IR (KBr, cm$^{-1}$) 3404, 2957, 2855, 1636, 1608, 1494, 1231; $^1$H NMR (400 MHz, DMSO) δ 11.31 and 10.70 (br s, 1H), 7.56 (s, 1H), 7.45 (d, J=7.6, 1H), 7.37–7.29 (m, 4H), 6.20 (d, J=7.5, 1H), 4.92–4.90 (m, 1H), 3.69 (s, 8H), 3.55–3.52 (m, 2H), 2.62 (s, 3H); LRMS (+ESI, M+H+) m/z 482; HPLC: 100% (230 nm); HRMS calcd for C$_{23}$H$_{24}$ClN$_7$O$_3$: 482.1707; found 482.1698.

EXAMPLE 9

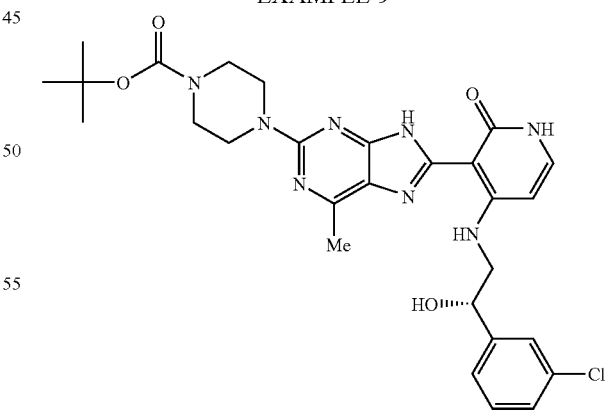

4-(8-{4-[2-(3–Chloro-phenyl)-2(S)-hydroxy-ethylamino]-2-oxo-1,2-dihydro-pyridin-3-yl}-6-methyl-9H-purin-2-yl)-piperazine-1-carboxylic acid t-butyl ester: To a solution of 4-[8-(4-chloro-2-oxo-1,2-dihydro-pyridin-3-yl)-6-methyl-9H-purin-2-yl]-piperazine-1-carboxylic acid t-butyl ester (200 mg, 0.448 mmol) in acetonitrile (10 mL) was added triethylamine (125 μl, 0.896 mmol) and (S)-2-amino-1-(3-chlorophenyl)-ethanol hydrochloride (99 mg, 0.493 mmol). The reaction mixture was stirred at 80° C. for 18 hours in a sealed tube and concentrated. The residue was dissolved in $CH_2Cl_2$ (50 mL) washed with $H_2O$ (2×30 mL), dried over $MgSO_4$ and concentrated. The crude material was purified by crystallization in hot MeOH (35 mL) to give the title compound as a beige solid. (0.197 g, 76%). HPLC 98%; LCMS ($^+$ESI, M+H$^+$) m/z 581; IR (KBr, cm$^{-1}$) 3419, 3271, 2975, 1696, 1496, 1232; $^1$H NMR (400 MHz, DMSO+$D_2O$) δ 10.79 (br s, 1H), 7.59–7.32 (m, 5H), 6.22 (d, J=7.6 Hz, 1H), 5.00 (br t, 1H), 3.73 (br s, 4H), 3.60 (m, 1H), 3.44 (br s, 4H), 2.58 (s, 3H); HRMS calcd for $C_{28}H_{33}ClN_8O_4$: 581.2391; found 581.2389.

EXAMPLE 10

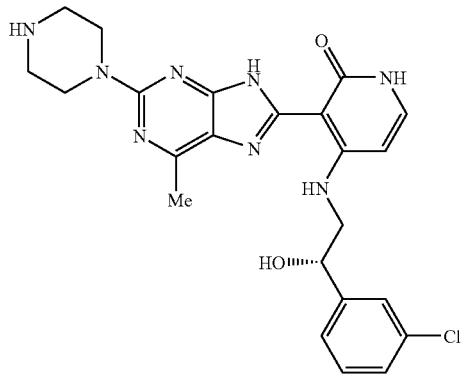

4-[2-(3–Chloro-phenyl)-2(S)-hydroxy-ethylamino]-3-(6-methyl-2-piperazin-1-yl-9H-purin-8-yl)-1H-pyridin-2-one: To a solution of 4-(8-{4-[2-(3–Chloro-phenyl)-2(S)-hydroxy-ethylamino]-2-oxo-1,2-dihydro-pyridin-3-yl}-6-methyl-9H-purin-2-yl)-piperazine-1-carboxylic acid tert-butyl ester (72 mg, 0.124 mmol) in $CH_2Cl_2$ (30 mL) was added benzenesulfonyl fonctionalized silica gel, 0.79 meq/g (7.2 g). The heterogeneous mixture was stirred at 23° C. for 16 hours. The solvent was removed by filtration and the silica gel was washed with a mixture of ammonia 2N in MeOH:$CH_2Cl_2$ (1:1, 20 mL). The ammoniac solution was evaporated in vacuo to give the title compound as a light yellow solid. (0.053 g, 89%). HPLC 98%; LCMS ($^+$ESI, M+H$^+$) m/z 481; IR (KBr, cm$^{-1}$) 3262, 2922, 1646, 1597, 1489, 1232; $^1$H NMR (400 MHz, DMSO+$D_2O$) δ 10.80 (br s, 1H), 7.59–7.29 (m, 5H), 6.23 (d, J=8.2 Hz, 1H), 5.00 (br t, 1H), 3.75 (br s, 4H), 3.62 (m, 1H), 2.89 (br s, 4H), 2.60 (s, 3H); HRMS calcd for $C_{23}H_{25}ClN_8O_2$: 480.1789; found 480.1804.

EXAMPLE 11

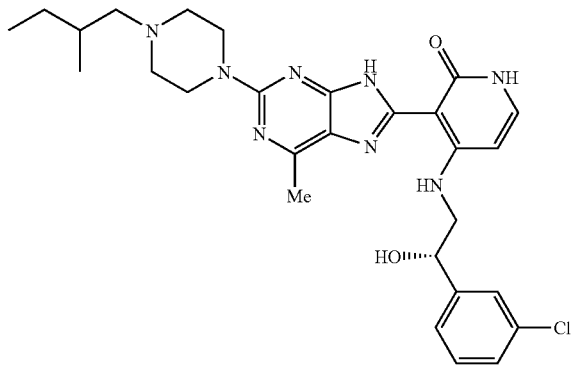

4-[2-(3–Chloro-phenyl)-2(S)-hydroxy-ethylamino]-3-{6-methyl-2-[4-(2-methylbutyl)-piperazin-1-yl]-9H-purin-8-yl}-1H-pyridin-2-one: To a solution of 4-[2-(3-chloro-phenyl)-2(S)-hydroxy-ethylamino]-3-(6-methyl-2-piperazin-1-yl-9H-purin-8-yl)-1H-pyridin-2-one (20 mg, 0.042 mmol) in a mixture of THF:DMF (1.5 mL:0.5 mL) was added glacial acetic acid (2.3 μl, 0.042 mmol) and 2-methylbutyraldehyde (12 μl, 0.117 mmol). The reaction mixture was stirred at 23° C. for 3 hours followed by the addition of NaBH(OAc)3 (24.9 mg, 0.117 mmol) to the reaction mixture and stirred for an additional 18 hours. MeOH (0.5 mL) was added and the solution was passed through a SCX cartridge (1 g, 0.79 meq/g, varian). The cartridge was eluted with MeOH (16 mL) and with 2N ammonia in MeOH (16 mL). The ammonia solution was evaporated in vacuo and the solid obtained was purified using a Shimadzu automated preparative HPLC System with the method described below. The solution was evaporated on a Savant Speedvac system to give the title compound as a light yellow solid. (14.2 mg, 62%). HPLC 95%; LCMS ($^+$ESI, M+H$^+$) m/z 551; IR (KBr, cm$^{-1}$) 3403, 2958, 1645, 1616, 1496, 1233; $^1$H NMR (400 MHz, DMSO+$D_2O$) δ 10.78 (brs, 1H), 7.60–7.29 (m, 5H), 6.22 (m, 1H), 4.97 (m, 1H), 3.80–3.55 (m, 6H), 2.52–2.15 (m, 8H), 1.75 (brs, 1H), 1.41 (brs, 1H), 1.15 (m, 1H), 0.86 (m, 6H).

Preparative HPLC Method:

Purification Method: Initial gradient (15% B, 85% A) ramp to final gradient (100% B, 0% A) over 7 minutes, hold for 3 minutes (100% B, 0% A)
Solvent A: 10% $CH_3CN$/90% $H_2O$/5 mmol $NH_4OAc$
Solvent B: 10% $H_2O$/90% $CH_3CN$/5 mmol $NH_4OAc$
Column: YMC C18 S5 20×100 mm column

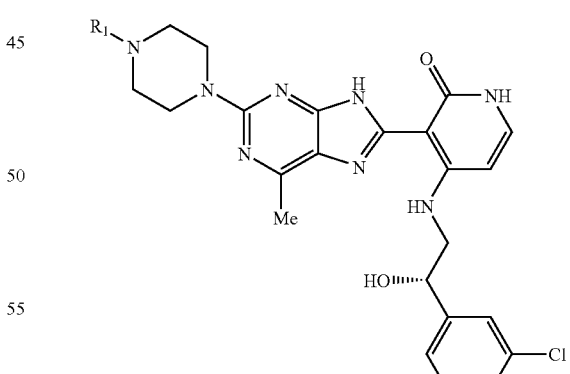

The corresponding aldehydes (Examples 12–21) were coupled with 4-[2-(3–Chlorophenyl)-2(S)-hydroxy-ethylamino]-3-6-methyl-2-piperazin-1-yl-9H-purin-8-yl)-1H-pyridin-2-one as described previously.

| Example | R₁ | Yield (%) | Purity HPLC | LCMS (⁺ESI, M + H⁺) |
|---|---|---|---|---|
| 12 | (1-methylimidazol-2-yl)methyl | 50 | >99 | 575 |
| 13 | (imidazol-2-yl)methyl | 65 | >99 | 561 |
| 14 | (pyridin-2-yl)methyl | 62 | >99 | 572 |
| 15 | (thiazol-2-yl)methyl | 58 | >99 | 578 |
| 16 | Et | 15 | >99 | 509 |
| 17 | benzyloxyethyl | 10 | >99 | 615 |
| 18 | cyclopropylmethyl | 55 | >99 | 535 |
| 19 | (2-ethoxycarbonylcyclopropyl)methyl | 61 | >99 | 607 |
| 20 | (1-methylpyrrol-2-yl)methyl | 29 | >99 | 574 |

-continued

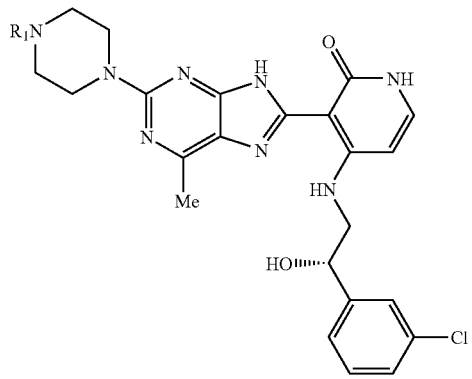

| Example | R₁ | Yield (%) | Purity HPLC | LCMS (⁺ESI, M + H⁺) |
|---|---|---|---|---|
| 21 |  | 22 | >99 | 589 |

EXAMPLE 22

Scheme IX

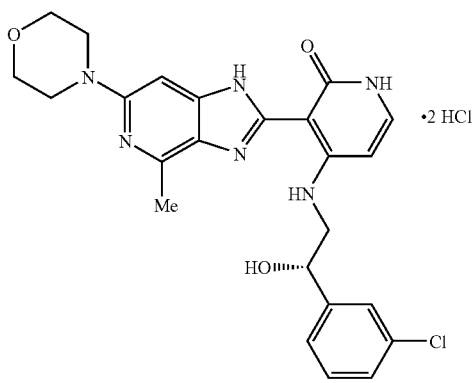

4-[2-(3–Chloro-phenyl)-2-hydroxy-ethylamino]-3-(4-methyl-6-morpholin-4-yl-1H-imidazo[4,5-c]pyridin-2-yl)-1H-pyridin-2-one bis-hydrochloride salt: To a solution of 2-(4-iodo-2-methoxy-pyridin-3-yl)-4-methyl-6-morpholin-4-yl-1H-imidazo[4,5-c]pyridine (75 mg, 0.17 mmol) in glacial acetic acid (3 mL) was added 3 mL of 11.6 M HCl in a pressure bottle. The vessel was sealed and heated to 70° C. for 16 hours. The reaction mixture was cooled and the vessel opened and concentrated in vacuo to give 66 mg of crude material which was used for the next step without purification. LCMS (⁺ESI, M+H⁺) m/z 346. To a solution of the crude pyridone (0.17 mmol) in a mixture of CH₃CN:DMSO (5 mL:1 mL) was added triethylamine (0.23 mL, 1.66 mmol) and (S)-2-amino-1-(3-chloro-phenyl)-ethanol hydrochloride (45 mg, 0.22 mmol). The reaction tube was sealed and the mixture stirred at 80° C. for 22 hours. The cooled mixture was concentrated in vacuo and the crude was purified by preparative HPLC (see method below) to give pure product (51 mg, 64%). A sample (20 mg) was dissolved in dioxane (3 mL) and EtOH (2 mL) and a solution of 1N HCl in EtOH was added to form the bis-hydrochloride salt. The solution was cooled to 0° C., filtrated and dried in vacuo to afford the above title salt as an white solid (19 mg, 83%): IR (KBr, cm⁻¹) 3179, 1622, 1532, 1435, 1234; ¹H NMR (400 MHz, DMSO-D₂O) δ 7.53 (br s, 1H), 7.42 (d, J=7.8, 1H), 7.36–7.27 (m, 3H), 7.17 (s, 1H), 6.18 (d, J=7.6, 1H), 4.95–4.93 (m, 1H), 3.78 and 3.36 (br t, 8H), 3.74–3.69 (m, 1H), 3.57–3.52 (m, 1H), 2.81 (s, 3H); LRMS (⁺ESI, M+H⁺) m/z 481; HPLC: 100% (230 nm).

What is claimed is:

1. A compound according to formula I:

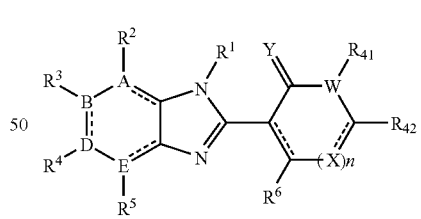

its enantiomers, diastereomers, pharmaceutically acceptable salts, hydrates, prodrugs and solvates thereof;
wherein
A, B, and are each C;
D is N;
X is selected from the group consisting of N or C wherein each of said N or C may be optionally substituted, independently, with $R^7$ and n is 0, 1, 2, or 3;
Y is selected from the group consisting of O and S;
W is selected from the group consisting of N, C, O, and S, provided that when W is O or S, $R^{41}$ is absent;
$R^3$ is morpholine $R^1$, $R^2$, $R^4$, $R^5$, $R^6$, $R^7$, $R^{41}$, and $R^{42}$ are each independently selected from the group consisting of H, $C_{1-6}$ alkyl, alkenyl, alkynyl, cycloalkyl, heterocycloalkyl, halo, amino, aminoalkyl, alkoxy, thioalkoxy, nitro, aryl, heteroaryl, alkoxyalkyl, thioalkoxyalkyl, aminoalkyl, aralkyl, heteroarylalkyl, heterocycloalkylalkyl, —CN, —$CO_2R^8$, —$CONR^9R^{10}$, —$CO_2NR^{11}R^{12}$, —$NR^{13}CONR^{14}R^{15}$, —$NR^{16}SO_2R^{17}$, —$SO_2NR^{18}R^{19}$, —$C(NR^{20})NR^{21}R^{22}$, —NH-Z, —NH-Z-aryl, and NH-Z-heteroaryl, or any two of $R^2$ and $R^3$, $R^3$ and $R^4$, or $R^4$ and $R^5$ can be taken together to form a heterocyclic ring having at least one nitrogen atom;

Z is selected from the group consisting of $C_1$–$C_6$ alkyl, cycloalkyl, alkenyl, cycloalkenyl, and alkynyl; Z optionally having one or more hydroxy, thiol, alkoxy, thioalkoxy, amino, halo, $NR^{23}S_2R^{24}$ groups and optionally incorporating one or more groups selected from —CO, —CNOH, —$CNOR^{26}$, —$CNNR^{27}$, —CNN-$COR^{28}$ or —$CNNSO_2R^{29}$;

$R^8, R^9, R^{10}, R^{11}, R^{12}, R^{13}, R^{14}, R^{15}, R^{16}, R^{17}, R^{18}, R^{19}, R^{20}, R^{21}, R^{22}, R^{23}, R^{24}$, and $R^{26}$ are independently selected from the group consisting of H, alkyl, alkenyl, alkynyl, cycloalkyl, cycloalkylalkyl, hydroxy, alkoxy, aryl, heteroaryl, heterocyclyl, heteroarylalkyl, and alkyl-$R^{25}$ wherein $R^{25}$ is alkenyl, hydroxy, thiol, alkoxy, thioalkoxy, amino, alkylamino, dialkylamino, aryl, heteroaryl, cyano, halo, heteroaryl, heterocyloalkyl, sulfoxy, sulfonyl, —$NR^{27}COOR^{28}$, —$NR^{29}C(O)R^{30}$, —$NR^{31}SOI_2R^{32}$, $SO_2NR^{31}R^{32}$, —$C(O)NR^{33}R^{34}$, and;

$R^{27}, R^{28}, R^{29}, R^{30}, R^{31}, R^{32}, R^{33}$ and $R^{34}$ are, independently, hydrogen, alkyl, or cycloalkyl.

2. The compound according to claim 1 wherein $R^1, R^2, R^4, R^5, R^{41}$, and $R^{42}$ are absent, H, or $C_1$ to $C_4$ alkyl; $R^3$ is morpholine.

3. The compound according to claim 2 wherein $R^6$ is —NH-Z-aryl.

4. The compound according to claim 3 wherein said aryl group is a phenyl group substituted at 1 or more positions on the ring.

5. The compound according to claim 4 wherein said substituent is a Br, F, Cl, or a methoxy group.

6. The compound according to claim 2 wherein $R^6$ is selected from the group consisting of H, 2-aminomethylpyridine, $NHCH_2CH(OH)$aryl, and $NHCH(CH_2OH)CH_2$aryl.

7. The compound according to claim 6 wherein said aryl is an optionally substituted phenyl.

8. The compound according to claim 7 wherein said phenyl is substituted with at least one of Br, Cl, F, alkoxy or —$NHSO_2CH_3$.

9. A compound selected from the group consisting of:
   4-[2-(3-Chloro-phenyl)-2(S)-hydroxy-ethylamino]-3-(6-methyl-2-morpholin-4-yl-9H-purin-8-yl)-1H-pyridin-2-one hydrochloride;
   4-[2-(3-Chloro-phenyl)-2-hydroxy-ethylamino]-3-(4-methyl-6-morpholin-4-yl-1H-imidazo[4,5-c]pyridin-2-yl)-1H-pyridin-2-one bis-hydrochloride.

10. A pharmaceutical composition comprising a compound according to claim 1 and a pharmaceutically acceptable carrier.

11. The pharmaceutical composition according to claim 10 further comprising at least one other anti-cancer agent selected from the group consisting of tamoxifen, toremifen, raloxifene, droloxifene, jodoxyfene, megestrol acetate, anastroxole, letrazole, borazole, exemestane, flutamide, nilutamide, bicalutamide, cyproterone acetate, goserelin acetate, luprolide, finasteride, trastuzumab, methotrexate, 5-fluorouracil, cytosine arabinoside, doxorubicin, daunamycin, epirubicin, idarubicin, mitomycin-C, dactinomycin, mithramycin, cisplatin, carboplatin, melphalan, chlorambucil, busulphan, cyclophosphamide, ifosfamide, thiotephan, vincristine, paclitaxel, docetaxel, etoposide, teniposide, amsacrine, irinotecan, topotecan, gefitinib, and erlotinibformulated as a fixed dose.

* * * * *

UNITED STATES PATENT AND TRADEMARK OFFICE
CERTIFICATE OF CORRECTION

PATENT NO.         : 7,189,716 B2
APPLICATION NO. : 10/751798
DATED                  : March 13, 2007
INVENTOR(S)        : Beaulieu et al.

It is certified that error appears in the above-identified patent and that said Letters Patent is hereby corrected as shown below:

On the Title Page, Item (74) "*Attorney, Agent, or Firm* - Elliot Korsen; Maureen S. Gibbons" should read: -- *Attorney, Agent, or Firm* - Elliott Korsen; Maureen S. Gibbons --

In Column 50, Line 58, "A, B, and are each C;" should read:

-- A, B, and E are each C; --

In Column 50, Line 66 "$R^3$ is morpholine" should read:

-- $R^3$ is morpholine; --

In Column 51, Line 16 "thioalkoxy, amino, halo, $NR^{23}S_2R^{24}$ groups and option-" should read: -- thioalkoxy, amino, halo, $\mathbf{NR^{23}SO_2R^{24}}$ groups and option- --

In Column 51, Line 29 "-$NR^{27}COOR^{28}$, -$NR^{29}C(O)R^{30}$, -$NR^{31}SOI_2R^{32}$," should read: -- -$NR^{27}COOR^{28}$, -$NR^{29}C(O)R^{30}$, $\mathbf{-NR^{31}SO_2R^{32}}$, --

In Column 52, Line 16 "2-one hydrochloride;" should read:

-- 2-one hydrochloride; and --

In Column 52, Lines 27-28 "raloxifene, droloxifene, jodoxyfene, megestrol acetate, anastroxole, letrazole, borazole, exemestane, flutamide, niluta-" should read:

-- raloxifene, droloxifene, idoxyfene, megestrol acetate, anastrozole, letrazole, borazole, exemestane, flutamide, niluta- --

UNITED STATES PATENT AND TRADEMARK OFFICE
CERTIFICATE OF CORRECTION

PATENT NO. : 7,189,716 B2
APPLICATION NO. : 10/751798
DATED : March 13, 2007
INVENTOR(S) : Beaulieu et al.

It is certified that error appears in the above-identified patent and that said Letters Patent is hereby corrected as shown below:

In Column 52, Line 36 "crine, irinotecan, topotecan, gefitinib, and erlotinibformu-"

should read: -- crine, irinotecan, topotecan, gefitinib, and eriotinib formu- --

Signed and Sealed this

Third Day of July, 2007

JON W. DUDAS
*Director of the United States Patent and Trademark Office*